(12) United States Patent
Lee et al.

(10) Patent No.: US 12,201,261 B2
(45) Date of Patent: Jan. 21, 2025

(54) CAPSULE ENDOSCOPE APPARATUS AND METHOD OF SUPPORTING LESION DIAGNOSIS

(71) Applicant: SUNGSHIN WOMEN'S UNIVERSITY INDUSTRY-ACADEMIC COOPERATION FOUNDATION, Seoul (KR)

(72) Inventors: Il-Gu Lee, Seoul (KR); So Eun Jeon, Seoul (KR); Ye Sol Oh, Gyeonggi-do (KR); Ji Eun Lee, Seoul (KR)

(73) Assignee: SUNGSHIN WOMEN'S UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 39 days.

(21) Appl. No.: 17/857,583

(22) Filed: Jul. 5, 2022

(65) Prior Publication Data

US 2023/0008154 A1    Jan. 12, 2023

(30) Foreign Application Priority Data

Jul. 7, 2021    (KR) .......................... 10-2021-0089323

(51) Int. Cl.
*A61B 1/00*    (2006.01)
*A61B 1/04*    (2006.01)
(Continued)

(52) U.S. Cl.
CPC .... *A61B 1/000094* (2022.02); *A61B 1/00006* (2013.01); *A61B 1/000096* (2022.02);
(Continued)

(58) Field of Classification Search
CPC .......... A61B 1/00097; A61B 1/000094; A61B 1/00006; A61B 1/000096; A61B 1/00016;
(Continued)

(56) References Cited

U.S. PATENT DOCUMENTS 3,670,722 A * 6/1972 Kosaka ................ A61B 1/0661
600/109
3,889,662 A * 6/1975 Mitsui ................ A61B 1/00181
385/119
(Continued)

FOREIGN PATENT DOCUMENTS

KR    20030039221 A    5/2003
KR    20030071821 A    9/2003
(Continued)

OTHER PUBLICATIONS

Application No. KR10-2021-0089323, Final Office Action, Mailed on Jul. 24, 2023, 7 pages.
(Continued)

*Primary Examiner* — John P Leubecker
*Assistant Examiner* — Jae Woo
(74) *Attorney, Agent, or Firm* — Kilpatrick Townsend & Stockton LLP

(57) ABSTRACT

Provided are a capsule endoscope apparatus for supporting a lesion diagnosis and a lesion diagnosis supporting method using the same. The capsule endoscope apparatus for supporting lesion diagnosis includes an imaging unit configured to capture one or more images of an inside of a body, a control unit configured to detect a suspected lesion region in the images and perform a precision diagnosis procedure when a suspected lesion region corresponding to a value equal to or greater than a certain threshold is detected, an image processing unit configured to process the images in the precision diagnosis procedure, and a communication
(Continued)

module configured to transmit and receive processed images to another capsule endoscope apparatus or a terminal by using a wireless communication method.

14 Claims, 30 Drawing Sheets

(51) Int. Cl.
*G06T 7/00* (2017.01)
*G06T 7/33* (2017.01)
*H04N 23/667* (2023.01)
*H04N 23/698* (2023.01)
*H04N 23/90* (2023.01)
*H04N 23/50* (2023.01)

(52) U.S. Cl.
CPC ...... *A61B 1/00016* (2013.01); *A61B 1/00097* (2022.02); *A61B 1/00181* (2013.01); *A61B 1/041* (2013.01); *G06T 7/0012* (2013.01); *G06T 7/33* (2017.01); *H04N 23/667* (2023.01); *H04N 23/698* (2023.01); *H04N 23/90* (2023.01); *G06T 2207/10068* (2013.01); *G06T 2207/30096* (2013.01); *H04N 23/555* (2023.01)

(58) Field of Classification Search
CPC ... A61B 1/00181; A61B 1/041; G06T 7/0012; G06T 7/33; H04N 23/667
See application file for complete search history.

(56) References Cited

U.S. PATENT DOCUMENTS

| | | | | |
|---|---|---|---|---|
| 7,319,781 | B2* | 1/2008 | Chen | A61B 1/000094 600/101 |
| 8,369,626 | B2* | 2/2013 | Nishimura | G06T 7/0002 382/128 |
| 8,617,058 | B2* | 12/2013 | Arneson | A61B 1/0004 600/160 |
| 8,830,307 | B2* | 9/2014 | Hirakawa | G06T 7/0012 348/45 |
| 9,854,958 | B1* | 1/2018 | Kukushkin | A61B 1/0005 |
| 11,055,843 | B2* | 7/2021 | Oh | G06N 3/049 |
| 2002/0099310 | A1* | 7/2002 | Kimchy | A61B 5/4255 600/587 |
| 2002/0109774 | A1* | 8/2002 | Meron | A61B 1/0676 382/128 |
| 2003/0139661 | A1* | 7/2003 | Kimchy | A61B 6/425 600/407 |
| 2004/0225223 | A1* | 11/2004 | Honda | A61B 1/041 128/920 |
| 2004/0263643 | A1* | 12/2004 | Imaizumi | A61B 1/0646 348/222.1 |
| 2005/0010083 | A1* | 1/2005 | Iriyama | A61B 1/0655 600/180 |
| 2006/0189843 | A1* | 8/2006 | Nakamura | A61B 1/041 600/109 |
| 2007/0161854 | A1* | 7/2007 | Alamaro | A61B 1/00194 600/109 |
| 2007/0167715 | A1* | 7/2007 | Shigemori | A61B 1/00016 600/407 |
| 2007/0225634 | A1* | 9/2007 | Ferren | A61B 17/12022 604/27 |
| 2008/0207997 | A1* | 8/2008 | Higgins | A61B 90/36 600/114 |
| 2009/0131746 | A1* | 5/2009 | Seo | G16H 30/20 600/101 |
| 2010/0152534 | A1* | 6/2010 | Kim | A61B 1/041 600/109 |
| 2010/0165088 | A1* | 7/2010 | Seo | A61B 1/0005 348/E7.085 |
| 2011/0255758 | A1* | 10/2011 | Nishimura | G06T 7/0002 382/128 |
| 2012/0264120 | A1* | 10/2012 | Toyota | G01N 33/57419 435/40.51 |
| 2012/0316421 | A1* | 12/2012 | Kumar | A61B 1/000094 600/407 |
| 2013/0072783 | A1* | 3/2013 | Hyde | A61B 6/5241 600/424 |
| 2014/0005477 | A1* | 1/2014 | Gupta | A61B 1/000094 600/109 |
| 2014/0296666 | A1* | 10/2014 | Rabinovitz | A61B 1/063 600/310 |
| 2019/0365325 | A1* | 12/2019 | Reiner | A61B 5/07 |
| 2020/0214636 | A1* | 7/2020 | Kimchy | A61B 5/14539 |
| 2021/0045621 | A1* | 2/2021 | Bae | A61B 1/00016 |
| 2021/0267475 | A1* | 9/2021 | Smirnov | A61B 1/041 |
| 2023/0008154 | A1* | 1/2023 | Lee | H04N 23/617 |

FOREIGN PATENT DOCUMENTS

| | | |
|---|---|---|
| KR | 20060117110 A | 11/2006 |
| KR | 20100069192 A | 6/2010 |
| KR | 20190103937 A | 9/2019 |
| KR | 102058192 B1 | 12/2019 |

OTHER PUBLICATIONS

Application No. KR10-2021-0089323, Office Action, Mailed on Feb. 3, 2023, 7 pages.

* cited by examiner

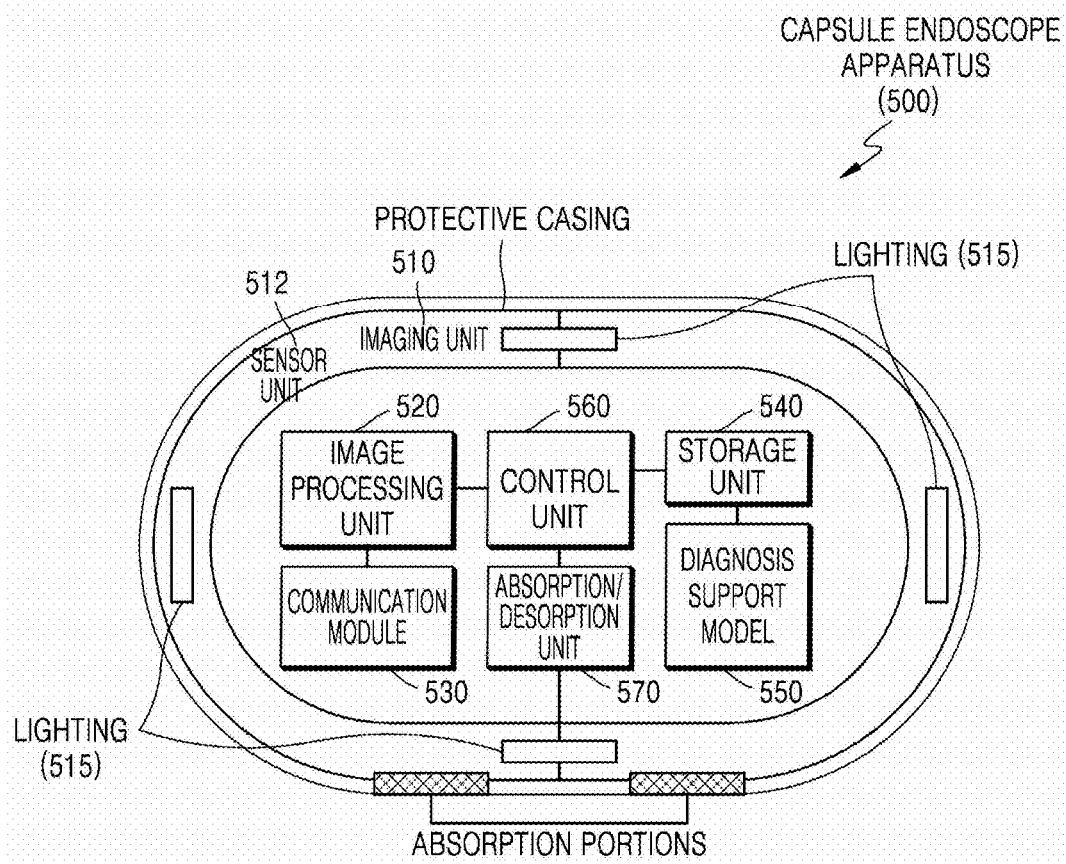

FIG. 10C
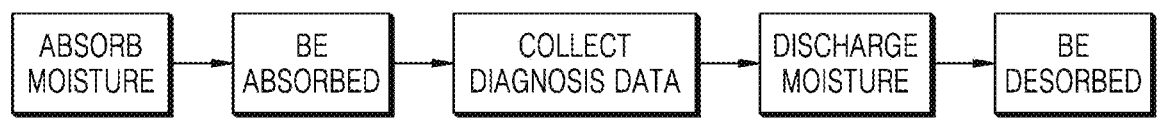
VACUUM ABSORPTION/DESORPTION OPERATIONS
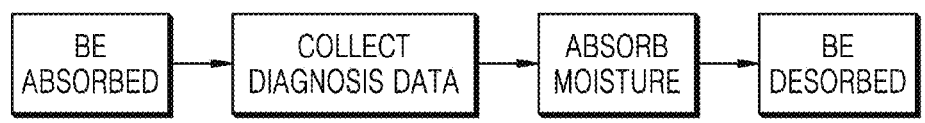
WET ABSORPTION/DESORPTION OPERATIONS

FIG. 11

| fold 1 | train set | test set | test set | test set | test set |
| --- | --- | --- | --- | --- | --- |
| fold 2 | test set | train set | test set | test set | test set |
| fold 3 | test set | test set | train set | test set | test set |
| fold 4 | test set | test set | test set | train set | test set |
| fold 5 | test set | test set | test set | test set | train set |

CAPSULE ENDOSCOPE-SERVER UNIDIRECTIONAL
COMMUNICATION STRUCTURE

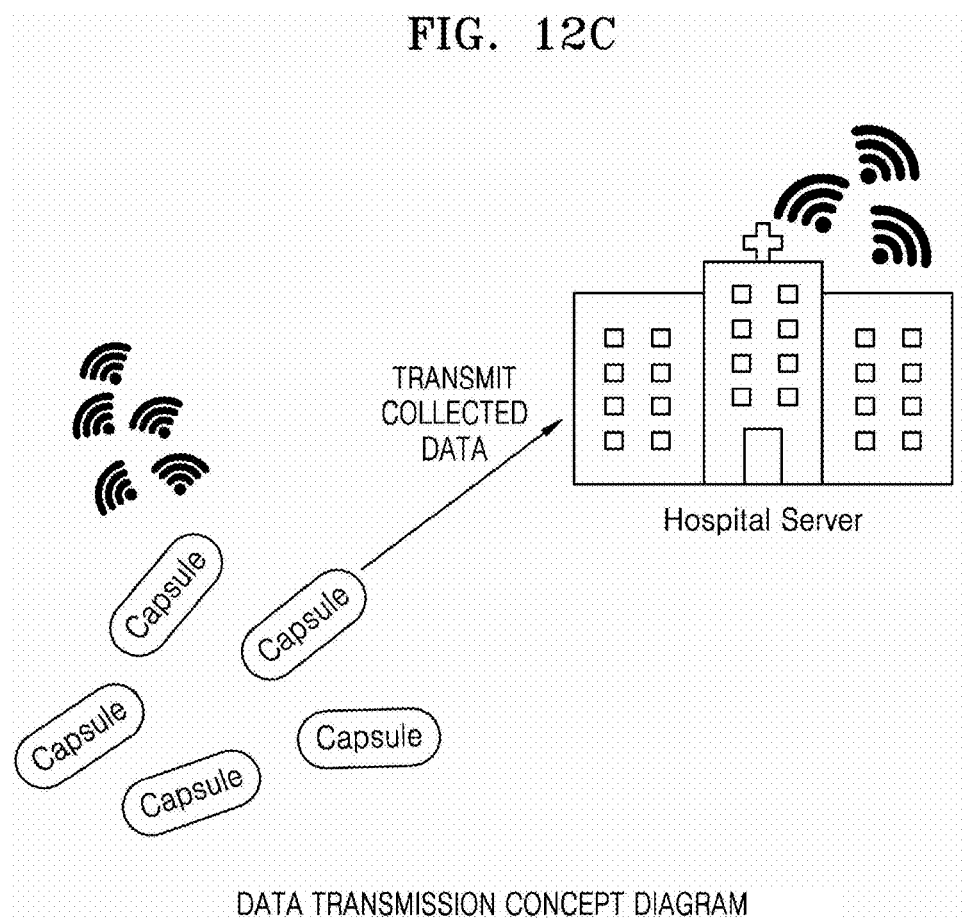

DATA TRANSMISSION STAGE EMPLOYING
END-TO-END ENCRYPTION VPN TECHNIQUE

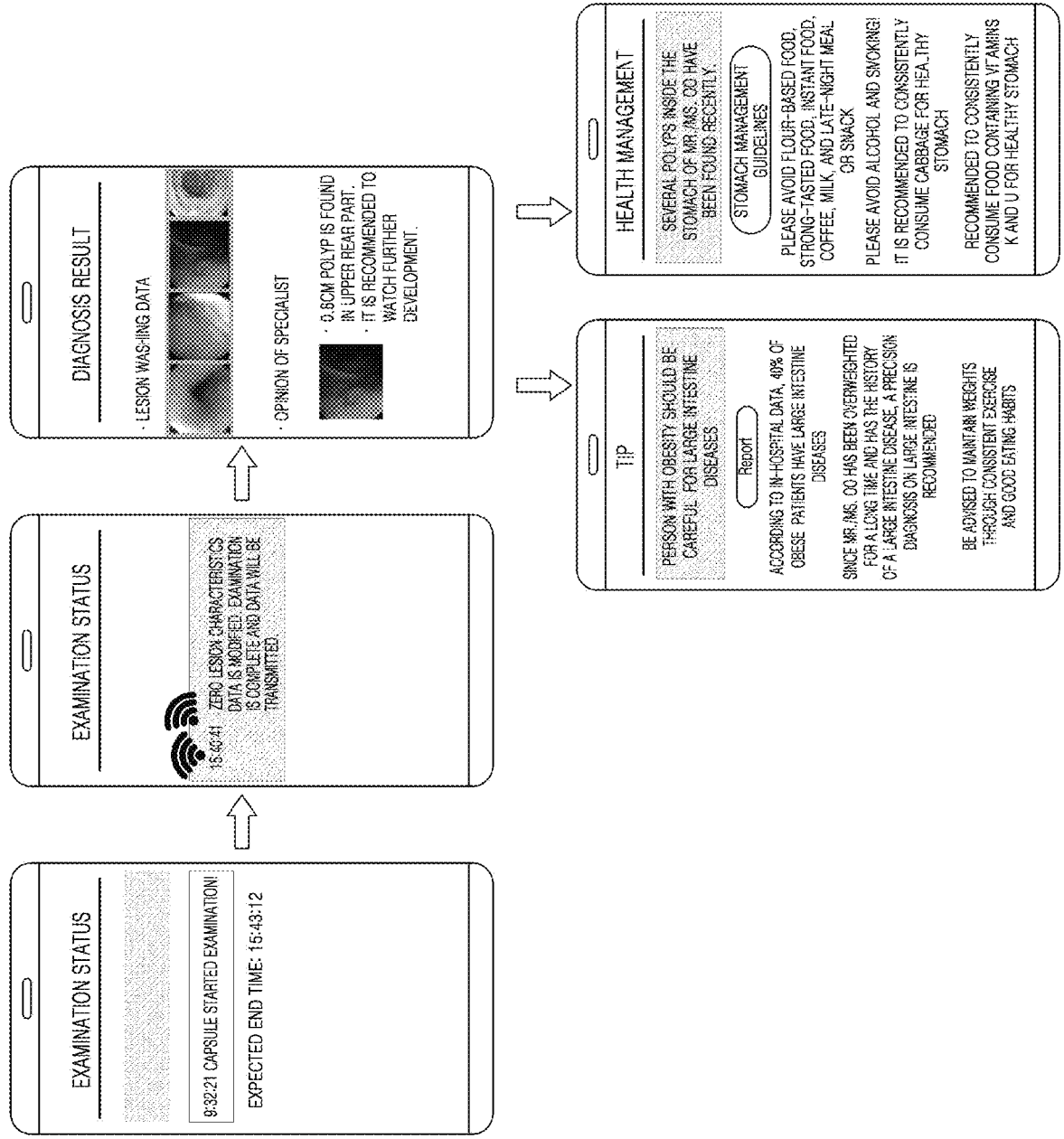

CAPSULE ENDOSCOPE APPARATUS AND METHOD OF SUPPORTING LESION DIAGNOSIS

CROSS-REFERENCE TO RELATED APPLICATION

This application is based on and claims priority under 35 U.S.C. § 119 to Korean Patent Application No. 10-2021-0089323, filed on Jul. 7, 2021, in the Korean Intellectual Property Office, the disclosure of which is incorporated by reference herein in its entirety.

BACKGROUND

1. Field

The present disclosure relates to a method of supporting lesion diagnosis by using a capsule endoscope apparatus.

2. Description of the Related Art

Conventional capsule endoscopes may be categorized into a first generation, a second generation, and a third generation. A first generation capsule endoscope is a currently commercialized capsule endoscope, wherein a capsule is moved by peristaltic movement of the intestine, and the accuracy of small intestine disease diagnosis is from about 60% to about 70%. However, since the first generation capsule endoscope relies on peristalsis, a second generation capsule endoscope has been developed to overcome limits of the first generation capsule endoscope. The second-generation capsule endoscope uses a magnetic field to overcome the movement limit and an examination is conducted by moving a capsule endoscope from the outside of the body by using a magnetic field. While the first-generation capsule endoscope and the second-generation capsule endoscopes were limited to examination, a more advanced third-generation capsule endoscope is above to evolve into a capsule endoscope capable of diagnosing and treating at the same time.

However, since a conventional capsule endoscope generally uses only one capsule, all functions such as imaging and treatment need to be included in one capsule. Since a capsule endoscope enters the body, there is a limit in the maximum size, and thus there are problems like a battery issue due to power consumption or difficulty of implementing multiple functions. Also, since it is difficult to control a posture and a location of a capsule endoscope inside the body, it is difficult to capture accurate images.

The present disclosure aims to fundamentally solve limits of the conventional capsule endoscope by using a plurality of capsule endoscopes. By dividing roles to a plurality of capsule endoscopes, the burden of each capsule endoscope may be reduced and blind spots in captured images may be reduced. Also, a function of controlling postures and locations of the capsule endoscope is provided.

SUMMARY

Provided are a capsule endoscope apparatus for supporting a lesion diagnosis and a lesion diagnosis supporting method using the same. The technical objects to be achieved by the present embodiment are not limited to the technical objects as described above, and other technical problems may be inferred from the following embodiments.

Additional aspects will be set forth in part in the description which follows and, in part, will be apparent from the description, or may be learned by practice of the presented embodiments of the disclosure.

According to an aspect of an embodiment, a capsule endoscope apparatus for supporting lesion diagnosis, the capsule endoscope apparatus includes an imaging unit configured to capture one or more images of an inside of a body, a control unit configured to detect a suspected lesion region in the images and perform a precision diagnosis procedure when a suspected lesion region corresponding to a value equal to or greater than a certain threshold is detected, an image processing unit configured to process the images in the precision diagnosis procedure, and a communication module configured to transmit and receive processed images to another capsule endoscope apparatus or a terminal by using a wireless communication method.

Here, the image processing unit may perform pre-processing on images captured by the imaging unit in the precision diagnosis procedure, and the control unit may further include a diagnosis unit configured to analyze a suspected lesion region of each body region and diagnose whether the suspected lesion region corresponds to a lesion.

Also, when it is determined to adjust brightness of an image as a result of the pre-processing, the control unit may adjust a lighting of the imaging unit.

The communication module may receive one or more processed first images from other capsule endoscope apparatuses in the precision diagnosis procedure, and the image processing unit may perform a process of registering a second image including information regarding the suspected lesion region with the one or more first images.

For example, the image processing unit may downsample the one or more first images to extract feature points and register the second image by matching the extracted feature points with features of a base image.

Also, the capsule endoscope apparatus may further include a sensor unit including at least one of a geomagnetic sensor, an acceleration sensor, and a timer sensor. Here, the control unit may calculate location information regarding body regions based on a sensing result of the sensor unit.

In another example, in the precision diagnosis procedure, the control unit may switch to a leader mode or a follow mode set in advance based on the location information regarding body regions, and the communication module may receive processed first images from another capsule endoscope apparatus when the capsule endoscope apparatus is in a leader mode and transmit processed first images to another capsule endoscope apparatus when the capsule endoscope apparatus is in a follow mode.

Here, the imaging unit may include multi-camera modules arranged at different locations to capture images having a plurality of viewpoints, and the image processing unit may register an omni-view image from the plurality of images having a plurality of viewpoints.

Also, the capsule endoscope apparatus may further include an adsorption/desorption unit capable of being adsorbed and desorbed to or from an inner wall of a body by absorbing moisture from the inner wall and discharging stored moisture.

According to an aspect of another embodiment, a method of supporting lesion diagnosis, the method includes capturing one or more images of an inside of a body, detecting a suspected lesion region in the images and performing a precision diagnosis procedure when a suspected lesion region corresponding to a value equal to or greater than a certain threshold is detected, processing the images in the precision diagnosis procedure, and transmitting and receiving processed images to or from another capsule endoscope apparatus or a terminal by using a wireless communication method.

Here, in the processing of the images, pre-processing may be performed on the captured images, and the method may further include analyzing a suspected lesion region for each body region and diagnosing whether the suspected lesion region corresponds to a lesion.

Also, the method may further include adjusting a lighting of an imaging unit when it is determined as a result of the pre-processing that brightness of images need to be adjusted.

In another example, the method may further include switching to a leader mode or a follow mode set in advance based on the location information regarding body regions, receiving processed first images from another capsule endoscope apparatus in the leader mode, and registering, with received one or more first images, a second image including information regarding the suspected lesion region.

Here, in the registering the second image, feature points may be extracted by down-sampling the first images and matching the extracted feature points with features of a basic image.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 5 is a diagram for describing components of a capsule endoscope apparatus according to an embodiment;

FIGS. 10A to 10D show examples of a method of moving and fixing a capsule endoscope apparatus to an inner wall to perform a precise diagnosis according to another embodiment;

FIG. 11 shows an example of a method by which a capsule endoscope apparatus according to an embodiment supports a lesion diagnosis;

FIGS. 12A to 12C show examples of a method by which a capsule endoscope apparatus performs wireless communication with another capsule endoscope apparatus or a terminal;

FIG. 16 is a conceptual diagram for describing providing a diagnosis result to a user through interconnection with a mobile platform according to another embodiment.

DETAILED DESCRIPTION

Figure 1:
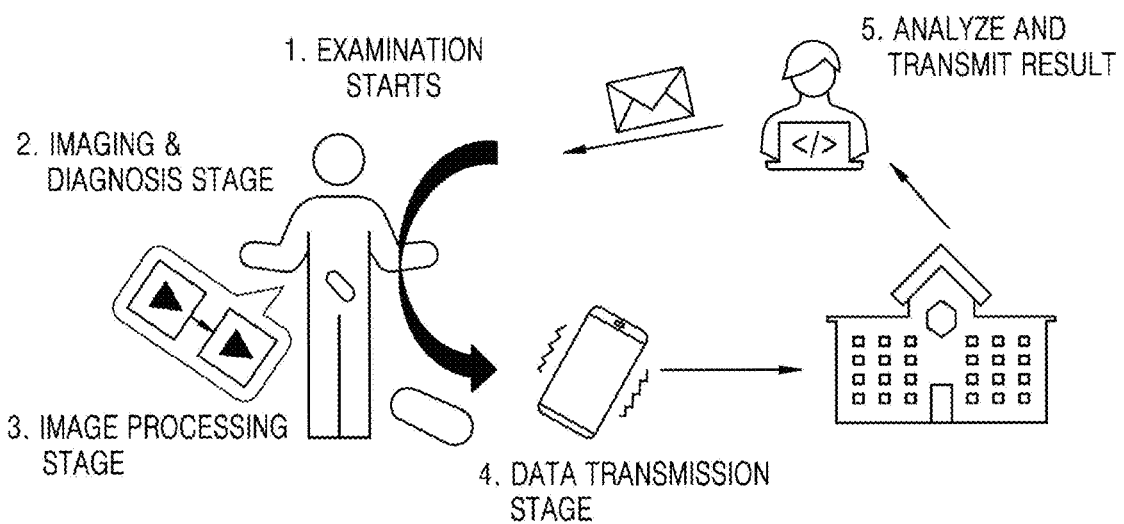
FIG. 1 shows an example of a lesion diagnosis supporting system using a capsule endoscope apparatus according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Unless defined otherwise, all terms (including technical and scientific terms) used herein may be used with the definitions commonly understood by one of ordinary skill in the art to which the present disclosure belongs. Also, terms defined in a commonly used dictionary are not to be interpreted ideally or excessively unless clearly defined in particular. The terms used herein are for the purpose of describing the embodiments and are not intended to limit the present disclosure. As used herein, the singular forms "a," "an" and "the" are intended to include the plural forms as well, unless the context clearly indicates otherwise.

It will be further understood that the terms "comprises" and/or "comprising" used herein specify the presence of stated components, operations, and/or devices, but do not preclude the presence or addition of one or more other components, operations, and/or devices.

A component included in one embodiment and a component having a common function may be described by using the same name in different embodiments. Unless otherwise stated, descriptions in one embodiment may be applied to other embodiments, and detailed descriptions may be omitted within the redundant range or within the range that may be clearly understood by one or ordinary skill in the art.

Hereinafter, embodiments of the present disclosure will be described in detail with reference to the accompanying drawings.

FIG. 1 shows an example of a lesion diagnosis supporting system using a capsule endoscope apparatus according to an embodiment. Referring to FIG. 1, the lesion diagnosis supporting system using a capsule endoscope apparatus according to the present disclosure may be largely divided into an imaging and diagnosis stage, an image processing stage, a data transmission stage, and a result analysis and transmission stage, after an examination starts.

A capsule endoscope is equipped with a camera and may be manufactured as a small device that may be swallowed by a user. An examination starts when a subject swallows a capsule endoscope through the mouth, and the capsule endoscope moves through regions in the body of the subject (user) and captures a video. For example, the capsule endoscope may take successive images at the rate from about 0.5 to about 6 frames per second. Here, the number of frames captured per second may vary according to the technological development. A video of a certain length may include a plurality of image frames, and detailed operations will be described below for each image frame, which is the unit of each video.

A conventional capsule endoscope moves passively by relying on intestinal peristalsis. Therefore, to supplement the movement, medical staffs have been performing examinations by using a method like moving a capsule endoscope by using a magnetic field from outside the body of a subject.

However, according to the present disclosure, a capsule endoscope apparatus may be utilized in an imaging and diagnosing stage and an image processing stage in improved manners as applicable to the prior art, and detailed operations of each stage will be described later.

After the capsule endoscope is discharged outside the body, related data transmission stage starts, and images processed by the capsule endoscope may be transmitted to a medical institution or a service platform supporting medical diagnosis through a user terminal. Thereafter, the medical institution or the service platform supporting medical diagnosis may analyze a diagnosis result of the capsule endoscope apparatus and transmit a result of the analysis to the user.

At this time, a capsule endoscope diagnosis process may be implemented to dispose the original data remaining in the capsule endoscope to protect personal information. However, embodiments of the present disclosure are not limited to the descriptions herein, and data storage and disposal may be implemented in other ways as occasions demand.

Here, the capsule endoscope may capture images of the inside of the internal organs of the subject (user) after being inserted into the body of the subject (user) until being discharged and may diagnose or support diagnosis of a lesion based on a diagnostic model learned in advance. Data obtained by the capsule endoscope may be utilized in the future as data for training diagnostic models by the medical institutions or the service platform supporting medical diagnostic services, and embodiments like mobile interconnection or a body map may also be implemented to provide more convenient services to a user (examinee). Detailed descriptions thereof will be given later with reference to FIGS. 15A, 15B and 16.

Figure 2:
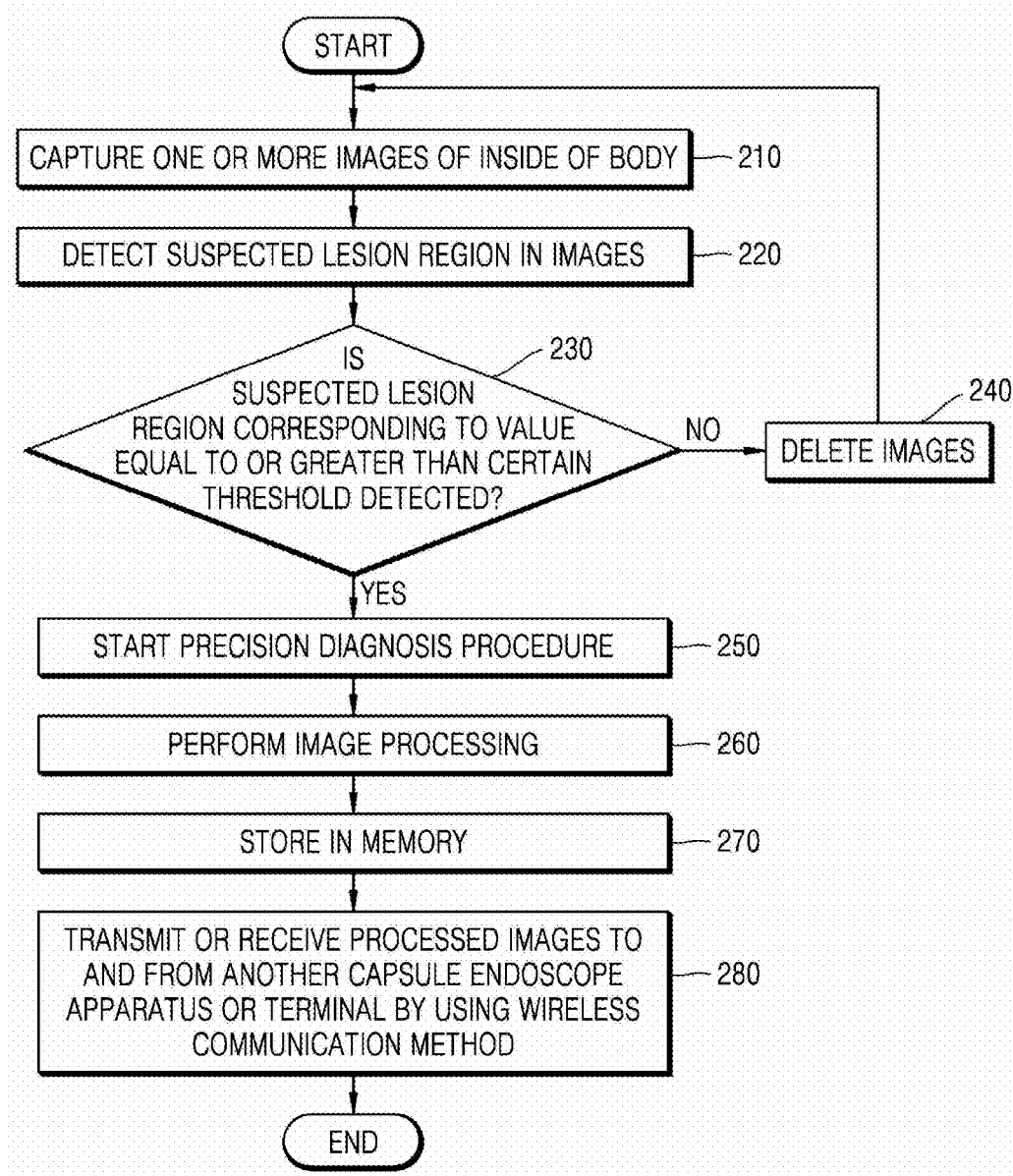
FIG. 2 is a flowchart of a method for diagnosing a lesion by using a capsule endoscope apparatus according to an embodiment.
Figure 3:
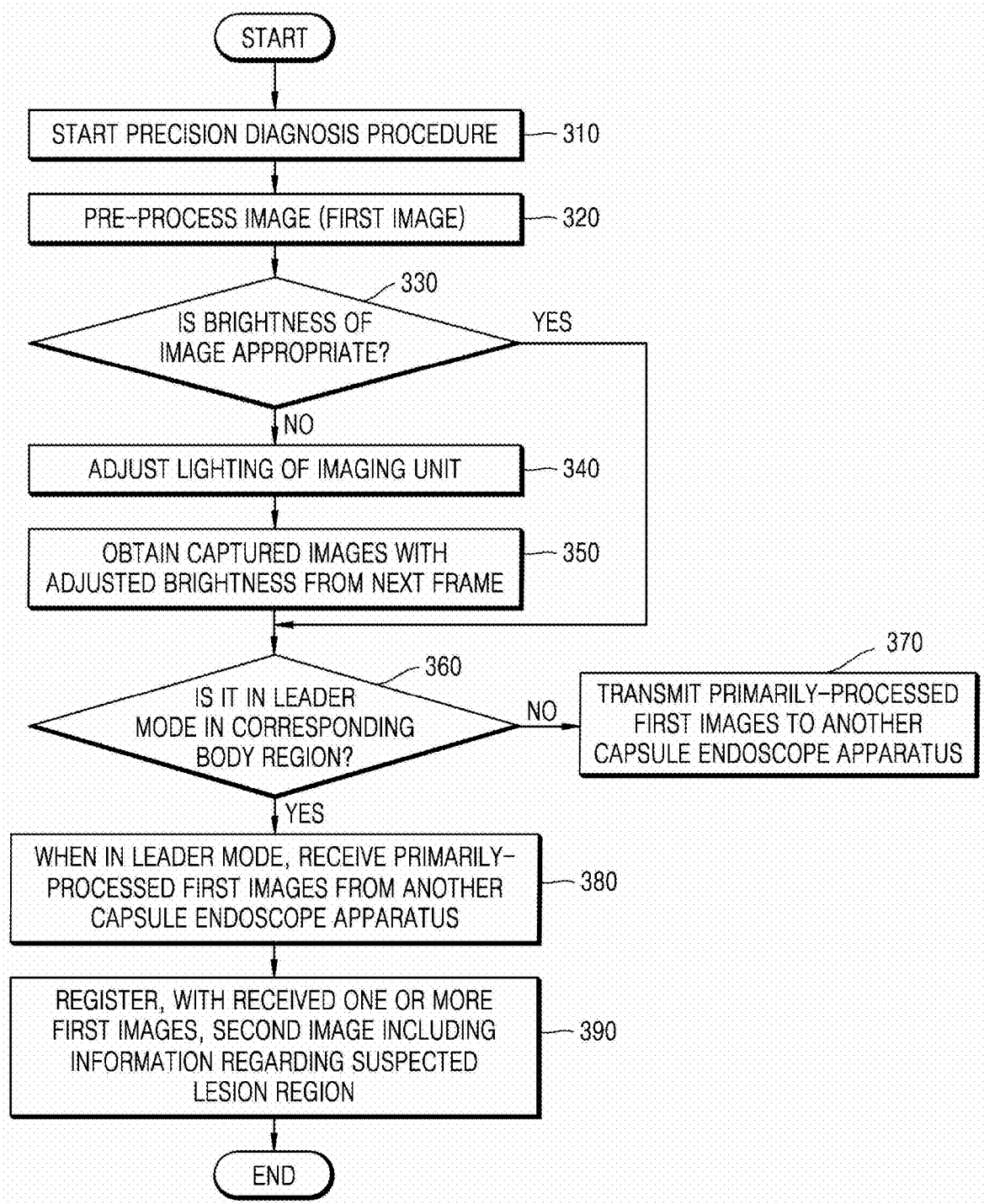
FIG. 3 shows an example of a method of performing a precision diagnosis procedure by the capsule endoscope apparatus.

FIG. 2 is a flowchart of a method for diagnosing a lesion by using a capsule endoscope apparatus according to an embodiment, and FIG. 3 shows an example of a method of performing a precision diagnosis procedure by the capsule endoscope apparatus. Referring to FIGS. 2 and 3, a capsule endoscope apparatus may diagnose a lesion through operations as described below.

First, the capsule endoscope apparatus may capture one or more images of the inside of the body (operation 210). Here, an image refers to one frame from a result of capturing a continuous moving picture. Therefore, images of a large number of frames may be stored while a moving picture is being recorded, and a diagnosis model according to the present disclosure may determine a suspected lesion region per image and diagnose a legion region based on a change in the suspected lesion region between consecutive frames.

Since the capsule endoscope apparatus is administered orally, images can be taken for each region of the body, such as the esophagus, the stomach, the small intestine, and the large intestine.

Previously, capsule endoscope apparatuses have been widely used only as an examination method specialized for the small intestine. The reason thereof is that, since the stomach or the large intestine has a relatively large inner diameter and a relatively complex structure as compared to the small intestine, the stomach or the large intestine cannot be sufficiently examined with the viewing angle of a capsule endoscope. For example, it is possible to partially observe the stomach or large intestine with a capsule endoscope. However, since a camera of the capsule endoscope captures images only in limited directions, a full examination of the stomach or large intestine is impossible. Also, since conventional capsule endoscopes are unable to perform close-up imaging or sample collection, the conventional capsule endoscopes have been mainly used as a standard method for examining the small intestine. It is known that the possibility of finding a disease of the small intestine with a conventional capsule endoscopy is from about 60% to about 70%.

On the other hand, the present disclosure discloses a capsule endoscope apparatus capable of moving and absorbing/desorbing for image quality enhancement and close-up imaging during a precision diagnosis procedure when the capsule endoscope apparatus detects a suspected lesion region, thus being distinguished from the prior art.

Next, the capsule endoscope apparatus may detect a suspected lesion region in an image (operation 220). The capsule endoscope apparatus may detect a suspected lesion region in an image through a previously learned diagnosis model and diagnose whether it is a lesion. For example, the capsule endoscope apparatus may extract feature values from an image and compare the feature values (data) with features of lesions stored in an existing DB, thereby detecting a suspected lesion region. Next, when a suspected lesion region corresponding to a certain threshold or greater value (operation S230), the capsule endoscope apparatus may initiate a precision diagnosis procedure (operation S250). The precision diagnosis procedure according to the present disclosure includes obtaining a high-quality image and performing image processing to increase the accuracy of a diagnosis result, and furthermore, a diagnosis is performed in an improved manner as compared to the prior art based on a user's medical history, characteristics of lesion regions in the body, and a possibility of being detected as lesions that are input to the diagnosis model in advance.

Here, the diagnosis model may use at least one algorithm of a non-linear regression or a deep neural network for network training. However, since there may be various other diagnosis models, methods of detecting and diagnosing lesions should not be construed as being limited to those described herein.

Even when the capsule endoscope apparatus detects a suspected lesion region, when the suspected lesion region is determined as being corresponding to a value less than or equal to a certain threshold according to the diagnosis model, an image related thereto may be deleted (operation 240) and an operation of capturing images of the inside of the body may be performed.

In the precision diagnosis procedure, the capsule endoscope apparatus may process images (operation 260). A detailed embodiment of processing images will be described below with reference to FIG. 3.

Referring to FIG. 3, when the capsule endoscope apparatus initiates a precision diagnosis procedure (operation 310), image pre-processing may be performed first (operation 320). Here, a pre-processed image may be referred to as a first image. At this time, when the brightness of the image is appropriate (operation 330), the method proceeds to a next operation. Otherwise, the capsule endoscope apparatus may adjust a lighting for capturing images (operation 340). As a result, images with adjusted brightness may be obtained from a next frame (operation 350).

Generally, an image processing method based on a deep neural network is capable of improving the image quality through various pre-processing, but it is difficult to extract useful data when the image quality of an original image for learning is significantly deteriorated. It will be especially difficult to extract useful data when a video is captured in a dark environment, such as inside the body. Therefore, according to the present disclosure, brighter images may be obtained by adjusting the intensity of a lighting, and thus better effective data regarding a suspected lesion region may be extracted.

Meanwhile, a lighting control may include not only increasing the brightness, but also adjusting the intensity of a lighting to an optimized intensity in consideration of the quality of obtained images and power consumption. For example, during the precision diagnosis procedure, the capsule endoscope apparatus may perform imaging by changing the intensity of a lighting in an imaging unit to various intensity levels and perform an optimal image quality enhancement by applying an average value for minimizing the loss function of image data according to each image intensity level.

In a next operation, the capsule endoscope apparatus may determine whether it is a leader mode is in a corresponding body region (operation 260). The capsule endoscope apparatus according to the present disclosure may have not only a diagnosis model specialized for the small intestine, but also diagnosis models specialized for various organs in the body. To this end, the capsule endoscope apparatus according to the present disclosure may obtain data regarding a movement speed, a direction, and a time from a geomagnetic sensor, an acceleration sensor, a timer, etc. and calculate an approximate location of the capsule endoscope apparatus in the body through a distance calculation. Such location information may be recorded as metadata for each image frame.

Generally, an approximate time during which the capsule endoscope apparatus moves in the body may also be determined within a certain range. Therefore, the capsule endoscope apparatus according to the present disclosure includes a timer and estimate an approximate location of the capsule endoscope apparatus in the body based on general time during which the capsule endoscope apparatus stays in each of the organs like the esophagus, the stomach, the small intestine, and the large intestine from a time point at which the capsule endoscope apparatus is administered orally.

According to another embodiment, the location of the capsule endoscope apparatus may be recorded by a scanning device in an external device and the time of the scanning device may be synchronized with the time of the capsule endoscope apparatus according to the present disclosure, thereby accurately estimating locations at which images are captured based on time information.

Also, when there are specific indicators indicating that the capsule endoscope apparatus is moving from one organ to another based on the characteristics of the organs like the esophagus, the stomach, the small intestine, and the large intestine, it may be determined through a diagnosis model based on captured images that the capsule endoscope apparatus entered a particular organ. However, the present disclosure is not limited thereto, and there may be various methods by which the capsule endoscope apparatus determines its location in the body other than those described herein.

In the case of a diagnostic method using a plurality of capsule endoscope apparatuses together, a capsule endoscope apparatus to play a leading role in a particular organ may be registered in advance. For example, when there are capsule endoscope apparatuses 1 to 3, an examiner may set a capsule endoscope apparatus 1 to serve as a leader in the small intestine, a capsule endoscope apparatus 2 to serve as a leader in the large intestine, and a capsule endoscope apparatus 3 to serve as a leader in the stomach. In this case, a collaborative process may be established by sharing the load for image processing applied to each capsule endoscope apparatus to the respective capsule endoscope apparatuses and sharing data acquired by the respective capsule endoscope apparatus through communication between the capsule endoscope apparatuses.

There may be various advantages of using a plurality of capsule endoscope apparatuses: a suspected lesion region from various viewpoints and various angles through the plurality of capsule endoscope apparatuses; and by registering one image with a plurality of images obtained by respective capsule endoscope apparatuses, a user may conveniently check approximate location, size, and shape of a suspected lesion region.

Referring to FIG. 3, when a capsule endoscope apparatus is in the leader mode in a corresponding body region, the capsule endoscope apparatus may receive primarily processed first images from other capsule endoscope apparatuses. At this time, each capsule endoscope apparatus may transmit and receive data unidirectionally or bidirectionally by using a wireless communication method. For example, when the capsule endoscope apparatus 1 is set in advance to serve as a leader in the small intestine and the capsule endoscope apparatus 1 detects a suspected lesion region in the small intestine and initiates a precision diagnosis procedure, the capsule endoscope apparatus 1 is in the leader mode in the small intestine and, in this case, may receive primarily processed first images from capsule endoscope apparatuses 2 and 3 (operation 380).

Next, the capsule endoscope apparatus 1 may register a second image including information regarding the suspected lesion region with one or more received first images (operation 390). For example, the capsule endoscope apparatus 1 may register one image (second image) with a plurality of images by down-sampling first images to extract feature points, and matching the extracted feature points with features of a base image. Here, the second image may include metadata like location information and information regarding the suspected lesion region like feature points of the suspected lesion region.

Meanwhile, referring to FIG. 3, when a capsule endoscope apparatus is not in the leader mode in a corresponding body region (operation 360), the corresponding capsule endoscope apparatus may be switched to a follow mode in the correspond body region and transmit primarily processed first image to another capsule endoscope apparatus (operation 370).

Referring back to FIG. 2, when the capsule endoscope apparatus completes an image processing (operation 260), the capsule endoscope apparatus may store processed images in a memory (operation 270). At this time, the capsule endoscope apparatus may store only processed images and destroy original data, thereby reducing the burden on memory storage.

For example, once a capsule endoscope apparatus is administered, it takes a considerable amount of time to be discharged through the digestive system of the human body. For example, when it takes from about 8 hours to about 9 hours for a single capsule endoscopy, from about 50,000 to about 60,000 images may be captured during the time. In the present disclosure, when an examination is finished, images stored by capsule endoscope apparatuses may be transmitted to a user terminal or a medical institution by using a wireless communication method, where only important image-processed data may be stored for efficiency of memory storage and data transmission. However, it is only an optional embodiment, and selection of data to be stored may be implemented differently as occasions demand and according to the development of technology.

Next, the capsule endoscope apparatus may transmit/receive processed images to another capsule endoscope apparatus or a terminal by using a wireless communication method (operation 280). The capsule endoscope apparatus may transmit data stored in a memory to a terminal when an examination is finished (discharged from the body). Here, the terminal may be a smartphone or a PC of an examiner or, according to another embodiment, may be a medical record management platform of a medical institution or a medical service providing platform of a device manufacturer.

An embodiment in which a capsule endoscope apparatus transmits/receives processed images by using a wireless communication method to another capsule endoscope will be described below with reference to FIGS. 4A and 4B.

Figure 4A:
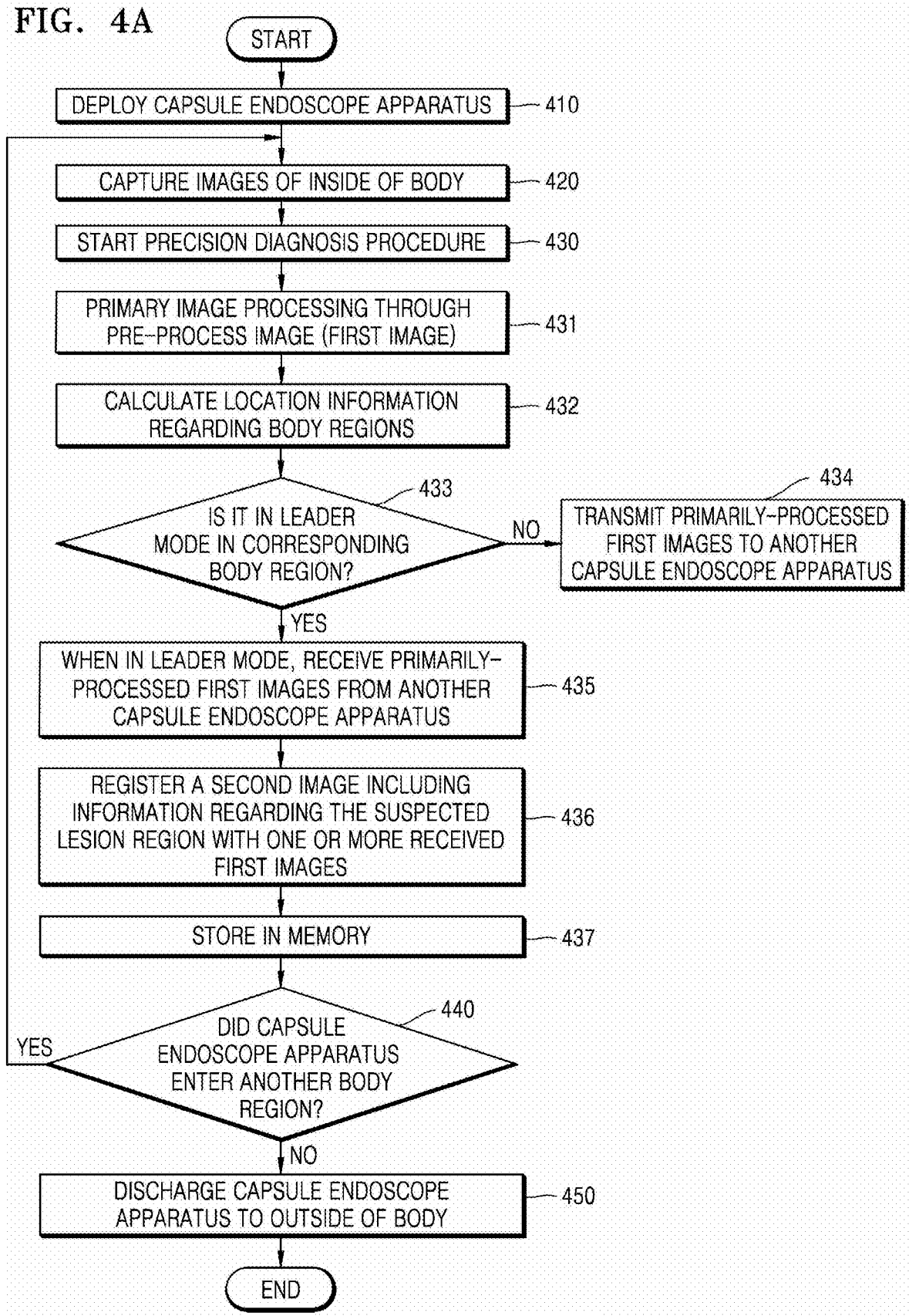
FIGS. 4A and 4B show an example of a method for performing a precision diagnosis procedure by capsule endoscope apparatuses according to another embodiment.
Figure 4B:
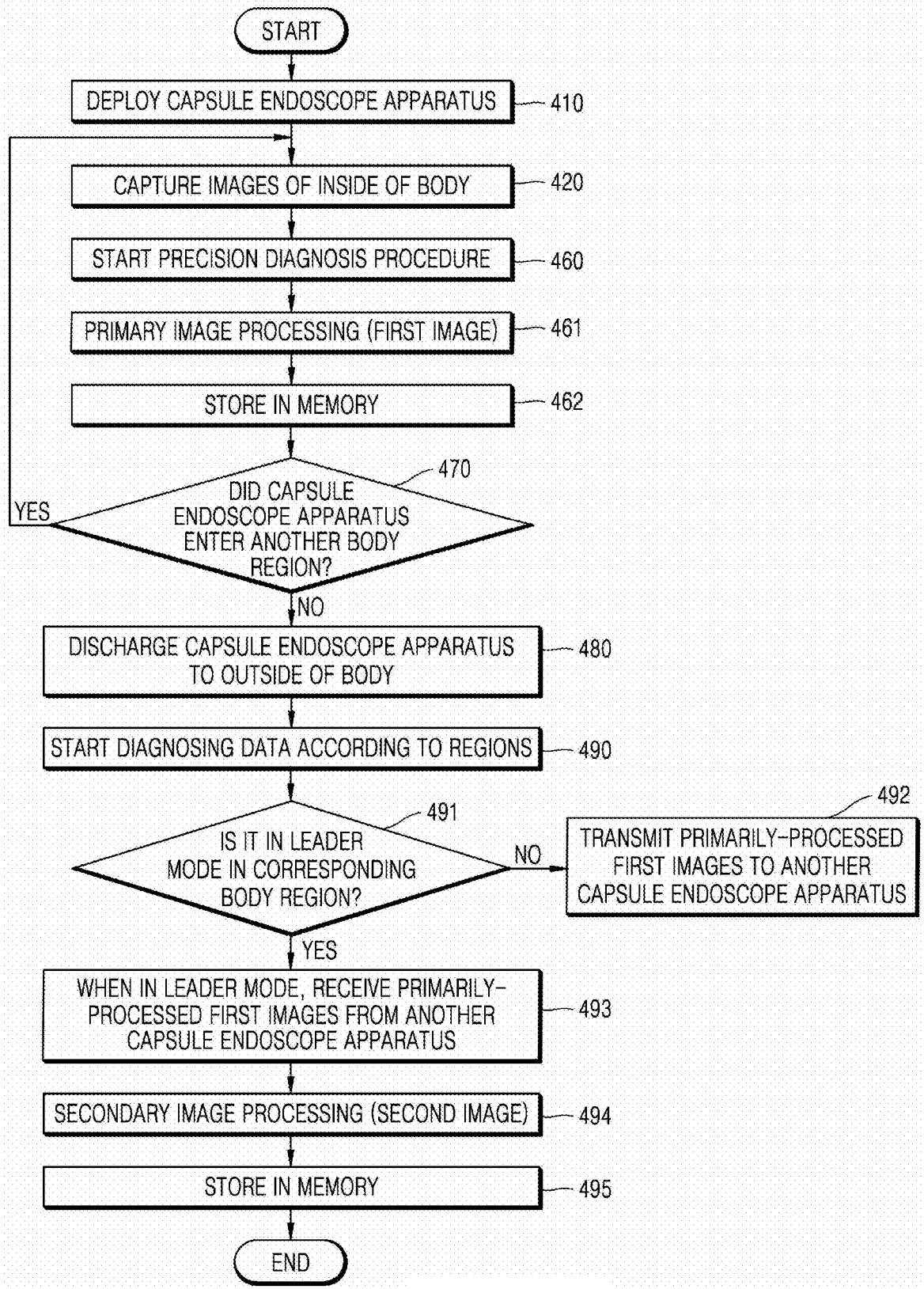

FIGS. 4A and 4B show an example of a method for performing a precision diagnosis procedure by capsule endoscope apparatuses according to another embodiment. In detail, embodiments may be described differently depending on whether a location at which a plurality of capsule endoscope apparatuses collect data is inside or outside the body.

FIG. 4A is an embodiment of a situation in which image processing is completed in the body. For example, a capsule endoscope apparatus is administered (operation 410), and images of the inside of the body may be captured (operation 420). Next, when a suspected lesion region is detected in images of the inside of the body and the detected suspected lesion region corresponds to a value equal to or greater than a certain threshold, the capsule endoscope may initiate a precision diagnosis procedure (operation 430). Next, the capsule endoscope apparatus may perform primary image processing through an image pre-processing process (operation 431). For convenience, primarily processed images may be referred to as first images.

Next, the capsule endoscope apparatus may calculate location information for respective body regions (operation 432) to determine an organ of the body in which the capsule endoscope apparatus is located and may determine whether the capsule endoscope apparatus is in the leader mode in the corresponding body region (operation 433). Here, when the capsule endoscope apparatus is in the follow mode, primarily processed first images may be transmitted to another capsule endoscope apparatus (operation 434).

When the capsule endoscope apparatus is in the leader mode, primarily processed first images may be received from other capsule endoscope apparatuses (operation 435). Next, the capsule endoscope apparatus may register a second image including information regarding the suspected lesion region with one or more received first images.

Here, the information regarding the suspected lesion region may include shapes of feature points or may be information regarding the possibility that the suspected lesion region determined in the precision diagnosis procedure is a lesion. Alternatively, the information regarding the suspected lesion region may be location information regarding a location at which the suspected lesion region is found.

The capsule endoscope apparatus may perform image processing to reinforce images such that a user may easily determine only information regarding a lesion from the second image, by registering one second image with a plurality of first images. For example, one image may include a fragmentary view of a lesion at a particular time point. However, when a plurality of images are registered, the 3-dimensional coordinates of the lesion that cannot be determined with one image may be calculated and expressed in one image, and thus schematic the approximate size, location, and shape of the lesion may be determined from the one image.

The capsule endoscope apparatus may perform image processing for processing images by using a previously learned diagnosis model and obtain a possibility that the suspected lesion region is a lesion. A deep learning model or a deep neural network model may be used as the diagnosis model. Here, although the term "diagnosis" is used, the final determination on a lesion is made by a human medical staff, and a diagnosis of a capsule endoscope apparatus referred to herein may have the meaning of "diagnosis support" as a reference model for the determination of the medical staff.

In the embodiment of FIG. 4A, when the capsule endoscope apparatus completes the image processing, a processed image(s) (second image(s)) may be stored in a memory (operation 437). In this case, there may be a plurality of processed second images, and the plurality of processed second images may be stored in the form of a continuous moving picture.

When the capsule endoscope apparatus passes a region in which the corresponding suspected lesion region is detected and the precision diagnosis procedure is completed, the capsule endoscope apparatus may determine again whether the capsule endoscope apparatus has entered another body region according to the location of the capsule endoscope apparatus (operation 440). When the capsule endoscope apparatus has entered another body region, the capsule endoscope apparatus may be switched back to a general examination operation for capturing images inside the body (operation 420). When the capsule endoscope apparatus is discharged outside the body instead of entering another body region (operation 450), the endoscope examination is terminated.

FIG. 4B is an embodiment of a situation in which image processing is completed outside the body. For example, a capsule endoscope apparatus may complete image processing after the capsule endoscope apparatus is discharged outside the body.

Referring to FIG. 4B, the capsule endoscope apparatus is administered (operation 410), and images inside the body may be captured (operation 420). Next, when a precision diagnosis procedure is initiated (operation 460), the capsule endoscope apparatus may perform a primary image processing on captured images (hereinafter referred to as first images). Referring to the embodiment of FIG. 3, the image processing here may be to obtain images with improved brightness by adjusting a lighting of an imaging unit in the precision diagnosis procedure in which a lesion is detected. In detail, an image with improved brightness may be obtained in a next frame rather than a corresponding image frame. However, since the environment for obtaining image frames obtained by the capsule endoscope apparatus is controlled and images with adjusted brightness may be obtained in a next successive frame, the image processing may be considered as the primary image processing.

In addition to the embodiment of FIG. 3, a method by which a capsule endoscope apparatus primary processes images may be implemented in various ways. For example, a capsule endoscope apparatus may pre-process an obtained image, obtain a possibility that a suspected lesion region is a lesion from pre-processed image, and tag the possibility as meta information regarding the corresponding image.

The capsule endoscope apparatus may diagnose whether the suspected lesion region is a lesion by comparing the suspected lesion region with pre-learned lesion data based on a result of the above image processing.

When the capsule endoscope apparatus completes the primary image processing and a diagnosis, corresponding data may be stored in a memory (operation 462), and, depending on whether the capsule endoscope apparatus has entered another body region (operation 470), the capsule endoscope apparatus may return to a general examination for capturing images inside the body. Similarly, when a suspected lesion region corresponding to a value equal to or greater than a certain threshold is detected, the precision diagnosis procedure may be performed again.

In the embodiment of FIG. 4B, the capsule endoscope apparatus may perform secondary image processing after the capsule endoscope apparatus is discharged (operation 480) to the outside of the body.

According to an embodiment, the capsule endoscope apparatus may start diagnosing data regarding each body region after being discharged to the outside of the body (operation 490). Next, a body region in which the capsule endoscope apparatus operated in the leader mode may be determined.

For a body region in which the corresponding capsule endoscope apparatus operates in the follow mode, primarily-processed first images stored in the memory of the corresponding capsule endoscope apparatus may be transmitted to another capsule endoscope apparatus operating in the leader mode (operation 492).

When a capsule endoscope apparatus is set to the leader mode in a particular organ, the primarily-processed first images may be received from other capsule endoscope apparatuses operating in the follow mode (operation 493) and an image processing operation may be performed thereon. For convenience, the image processing may be referred to as secondary processing, and secondarily-processed images may be referred to as second images (operation 494).

According to an embodiment, the secondary processing may be a processing of registering a second image including information regarding the suspected lesion region with one or more first images received from another capsule endoscope apparatus. For example, the capsule endoscope apparatus may register a second image by down-sampling one or more first images to extract feature points, and matching the extracted feature points with features of a base image.

Next, the capsule endoscope apparatus may store processed images in the memory and terminate the examination.

Flowcharts of methods for performing image processing inside and outside the body have been described above with reference to FIGS. 4A and 4B. However, the above descriptions relate to image processing that may be performed in the environment in which a plurality of capsule endoscope apparatuses cooperate with each other. Since a capsule endoscope apparatus may be used alone, detailed descriptions thereof will be given below with reference to FIG. 5.

FIG. 5 is a diagram for describing components of a capsule endoscope apparatus according to an embodiment. According to an embodiment, a capsule endoscope apparatus 500 may include an imaging unit 510, an image processing unit 520, a storage unit 540, a diagnosis support model 550, and a control unit 560, and may further include a sensor unit 512, a lighting 515, an adsorption/desorption unit 570, etc.

The imaging unit 510 may capture one or more images of the inside of the body. The imaging unit may obtain successive images at a rate from about 0.5 frames per second (FPS) to about 6 FPS, and, when technology is further developed, the imaging unit may be equipped with a camera capable of obtaining more frames per second.

According to another embodiment, the camera of the imaging unit may be a multi-camera module supporting omni-view. For example, the omni-view camera module may capture images of the inside of the body image with a wider field of view than a single camera, thereby resolving the limitations of the existing capsule endoscopes regarding imaging blind spots. For example, the omni-view camera may use one or two omni-view lenses, or a multi-camera module in which more cameras are mounted may be used.

Although the imaging unit of the present disclosure may use a single camera, when a plurality of camera modules are attached or the imaging unit is implemented in a structure capable of photographing in multiple directions or all directions, the reliability and the accuracy of an examination for detecting lesions may be improved. As an embodiment thereof, a method of obtaining a video having a viewing angle of up to 360 degrees will be described below.

Figure 6A:
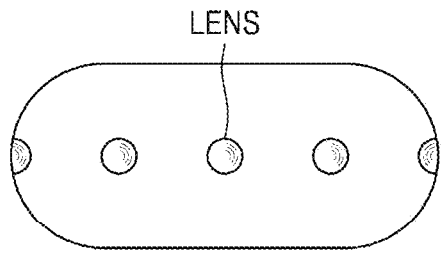
FIGS. 6A to 6D show examples of a camera module of a capsule endoscope apparatus according to an embodiment.

Referring to FIG. 6A, an imaging unit may be an example in which a plurality of camera lenses are attached to capture images in all directions (360 degrees) in the form of a spherical surface. For example, 360-degree imaging may be implemented by attaching a display module including a plurality of cameras having a wide viewing angle.

Figure 6B:
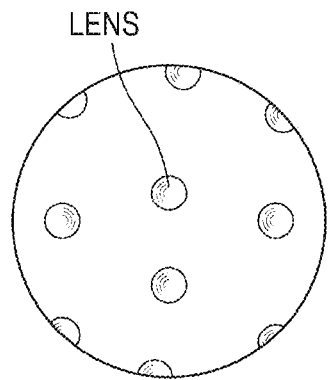

Referring to FIG. 6B, an imaging unit may capture images 360 degrees in vertical directions by attaching a plurality of wide-angle lenses. In this case, captured images having a wider viewing angle in the vertical direction than those in FIG. 6A may be obtained.

Figure 6C:
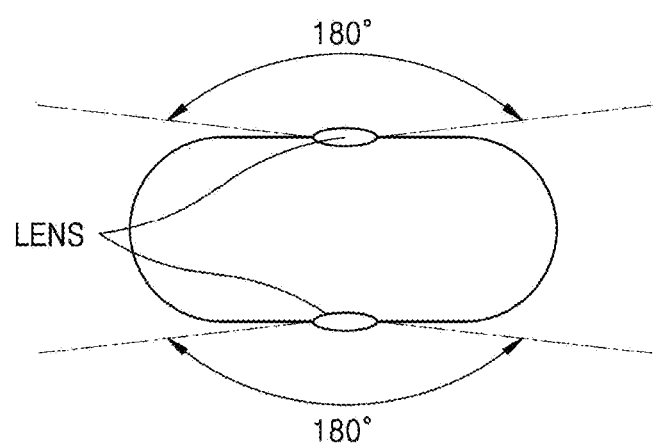

Referring to FIG. 6C, even lenses that are not wide-angle lenses may be attached on two long surfaces of a capsule, thereby implementing an omni-view video covering 360 degrees omnidirectional views. However, in this case, since each lens does not cover exactly 180 degrees, there may be some blind spots.

Figure 6D:
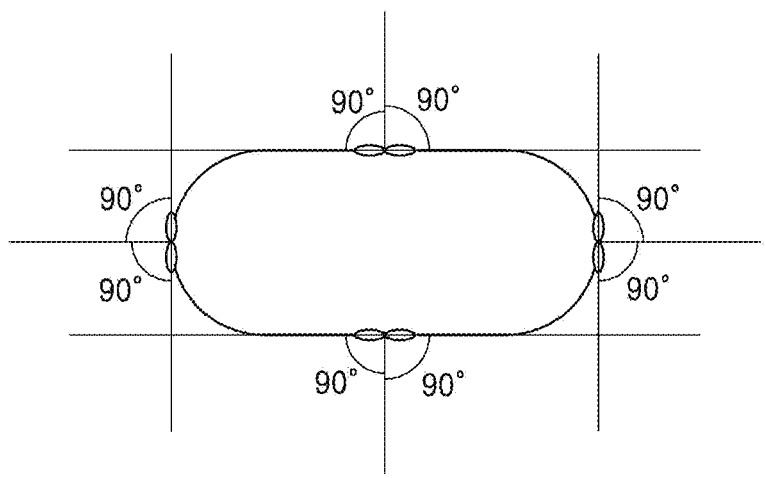

To complement the problem, referring to FIG. 6D, a 360-degree viewing angle may be realized by mounting a plurality of camera modules. Referring to FIG. 6D, when camera modules each having the viewing angle of 90 degrees are used, eight camera modules may be attached to implement a 360-degree viewing angle.

However, this is only an embodiment, and the present disclosure is not limited to the numbers of cameras described above. Changes only in the camera locations and directions may be considered as implementations within the scope of the present disclosure.

Figure 7:
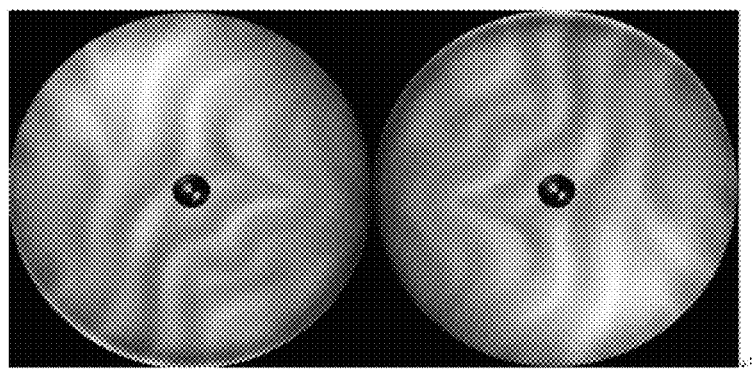
FIG. 7 shows an example of an omni-view image which is obtained by a capsule endoscope apparatus according to another embodiment by using a 360-degree camera, or which is registered with a plurality of images obtained through a plurality of cameras.

FIG. 7 is an example of an image that may be obtained by using a camera having 360-degree viewing angle. For example, a panoramic image capturing method may be implemented with 360-degree viewing angle by using a dome-type camera based on curved lenses. In this case, when light is incident on lenses, reflection from the inside is received as a 360-degree horizontal field of view, and thus images may be captured in all directions.

The lighting 515 is disposed near the imaging unit 510, and on/off and intensity thereof may be controlled by the control unit 560. Referring to FIG. 5, it may be seen that four lightings 515 are arranged at a constant interval. However, it is merely an embodiment, and the number and the arrangement of lightings are not limited thereto.

The sensor unit 512 may include a geomagnetic sensor, an acceleration sensor, a timer, etc. The control unit 560 may calculate location information regarding the capsule endoscope apparatus 500 based on data obtained from the sensor unit 512.

The advantage of the present disclosure is that a plurality of capsule endoscope apparatuses may cooperate with one another to obtain images of a suspected lesion region from various viewpoints and fields of view. In this case, when a plurality of capsule endoscope apparatuses are used in one examination, allocation of roles to the respective capsule endoscope apparatuses and a separate process for processing data are needed. Detailed descriptions thereof will be given later with reference to FIGS. 8A to 8C.

Also, a capsule endoscope apparatus according to the present disclosure may not simply move passively by peristalsis of the digestive system, but may include a moving means and adsorption/desorption means that may be attached at specific locations. Here, the capsule endoscope apparatuses may perform communication with one another in relation to information regarding their locations, settlement, and movement to a next region.

Figure 8A:
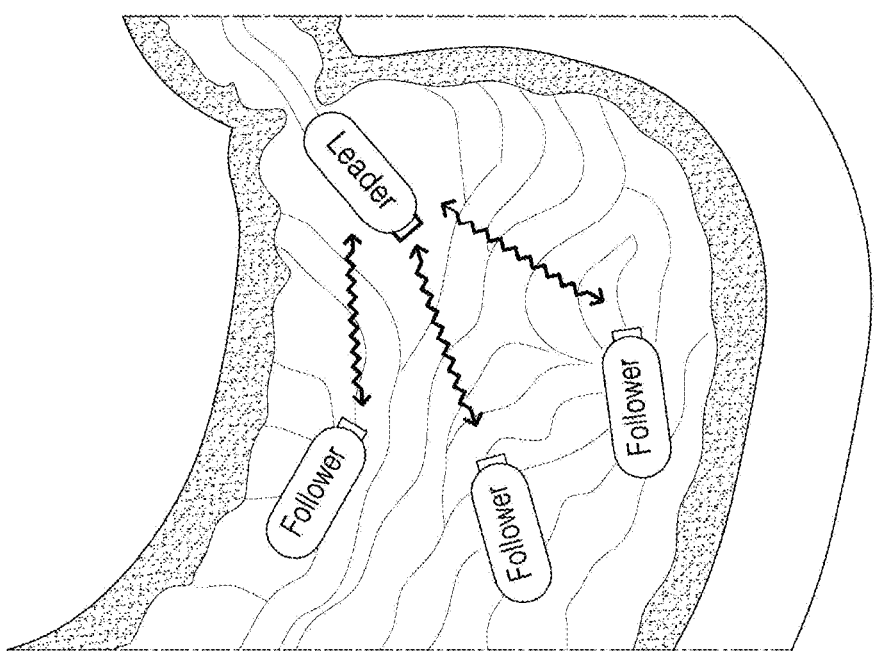
FIGS. 8A to 8C show examples for a collaborative process between a plurality of capsule endoscope apparatuses according to an embodiment.
Figure 8B:
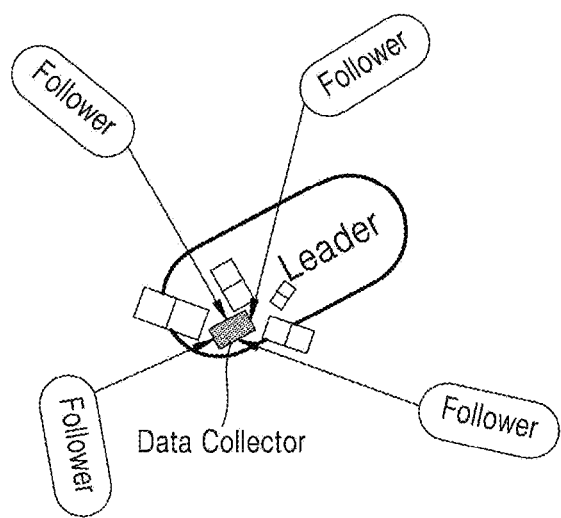

For example, referring to FIGS. 8A and 8B, there may be one leader capsule endoscope apparatus and three follower capsule endoscope apparatuses in the stomach. According to an embodiment, in the present disclosure, when a capsule endoscope apparatus moves in a floating manner in the body during a general examination, and, when it is determined that an intensive diagnosis is needed and a precision diagnosis procedure therefor is initiated, the capsule endoscope apparatus may be settled at a corresponding location for further observation of a suspected lesion region.

For example, when images are received from a plurality of capsule endoscope apparatuses, a capsule endoscope apparatus operating in the leader mode may determine that a corresponding region needs to be precisely diagnosed based on the number of received images. Also, the capsule endoscope apparatus operating in the leader mode may instruct itself and the other capsule endoscope apparatuses to be settled. As described above, a leader capsule endoscope apparatus and follower capsule endoscope apparatuses may perform inter-capsule communication and, through the inter-capsule communication, may transmit/receive images, share location information, and determine settlement location according to an instruction of the leader capsule endoscope apparatus.

Figure 8C:
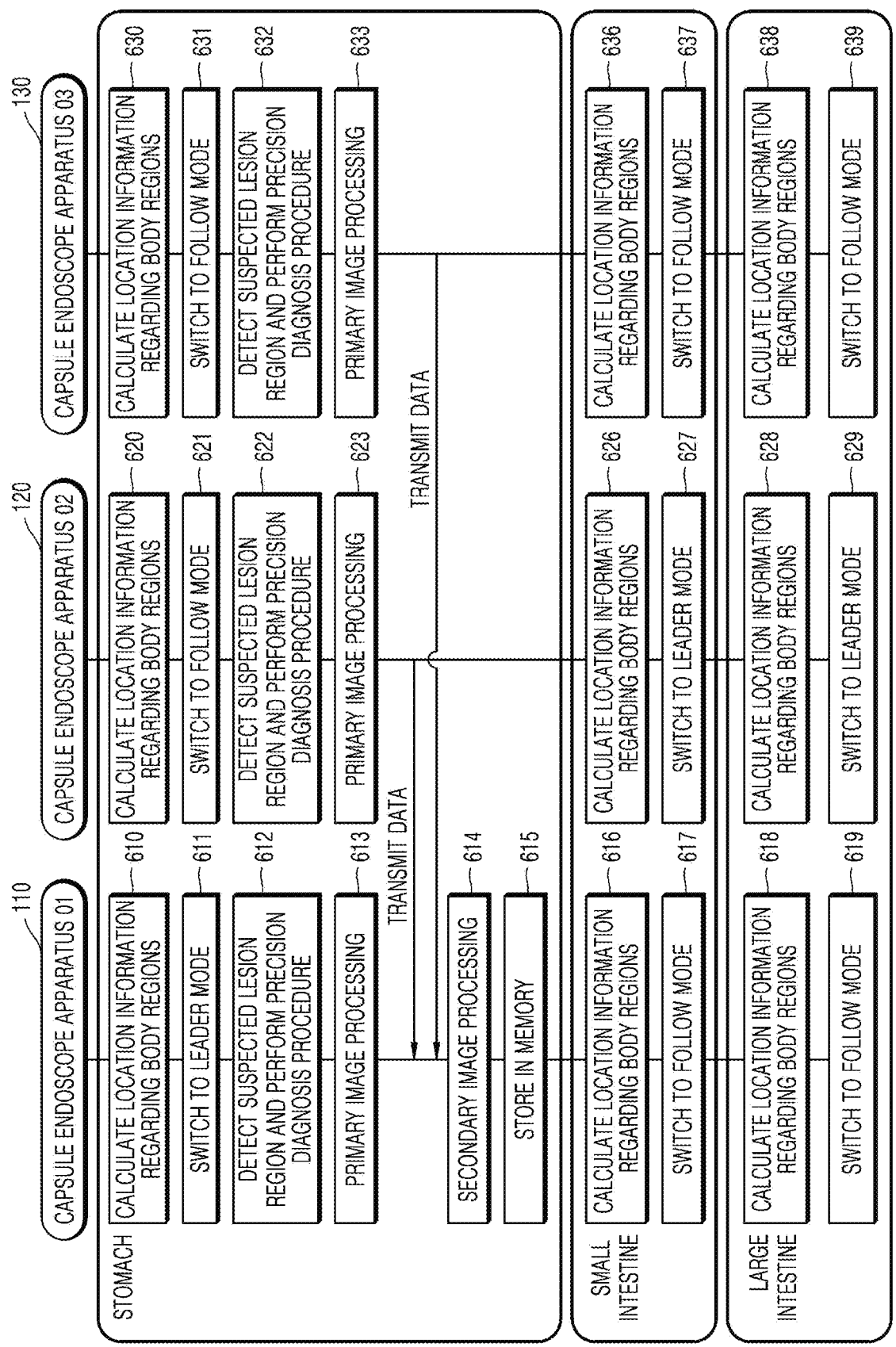

FIG. 8C is a diagram for describing how a capsule endoscope apparatus 01 110, a capsule endoscope apparatus 02 120, and a capsule endoscope apparatus 03 130 each process data for each body region.

Referring to FIG. 8C, it will be assumed that the capsule endoscope apparatus 01 110 operates in the leader mode in the stomach, the capsule endoscope apparatus 02 120 operates in the leader mode in the small intestine, the capsule endoscope apparatus 03 130 operates in the leader mode in the large intestine, and a suspected lesion region is detected in the stomach.

The capsule endoscope apparatus 01 110 may calculate location information regarding body regions (operation 610), and, when it is determined that the current body region is the stomach, the capsule endoscope apparatus 01 110 may be switched to the leader mode (operation 611). Then, when a suspected lesion region is detected, a precision diagnosis procedure may be performed (operation 612). At this time, once the suspected lesion region is detected, the capsule endoscope apparatus 01 110 may immediately perform primary image processing in relation to the suspected lesion region (operation 613). Also, when data is received from the capsule endoscope apparatus 02 120 and the capsule endoscope apparatus 03 130, the capsule endoscope apparatus 01 110 may register one second image with one or more first images received from the other capsule endoscope apparatuses. Here, the second image may include information regarding the suspected lesion region. After the capsule endoscope apparatus 01 110 performs the secondary image processing (operation 614) as described above, the capsule endoscope apparatus 01 110 may store a result thereof in a memory (the storage unit 540). Thereafter, the capsule endoscope apparatus 01 110 performs a general examination procedure after passing the region in which the suspected lesion region is detected, calculates location information regarding body regions (operation 616), and, when the location of the capsule endoscope apparatus 01 110 in the body is determined as the small intestine, is switched to the follow mode. Here, images are captured continuously and independently of the mode change. However, the memory may be managed by deleting images captured during a general examination without separately storing them. In the same regard, the capsule endoscope apparatus 01 110 may calculates location information regarding body regions (operation 618), may be switched to the follow mode (operation 619) when the location of the capsule endoscope apparatus 01 110 is the large intestine, and, when no suspected lesion region is detected, may perform a general examination procedure.

Meanwhile, the capsule endoscope apparatus 02 120 and the capsule endoscope apparatus 03 130 may also calculate location information regarding body regions (operations 620 and 630) and, when a current body region is determined as the stomach, may be switched to the follow mode (operations 621 and 631). Next, when a suspected lesion region is detected, the capsule endoscope apparatus 02 120 and the capsule endoscope apparatus 03 130 perform a precision diagnosis procedure (operations 622 and 632). At this time, the capsule endoscope apparatuses 02 120 and the capsule endoscope apparatus 03 130 perform primary image processing (operations 623 and 633) and transmit primarily-processed images to the capsule endoscope apparatus 01 110 operating in the leader mode. Although the capsule endoscope apparatus 02 120 and the capsule endoscope apparatus 03 130 operate in the leader mode in the small intestine and the large intestine, respectively, no suspected lesion region is detected, and thus the capsule endoscope apparatus 02 120 and the capsule endoscope apparatus 03 130 may capture images in the general examination mode.

Referring back to FIG. 5, the control unit 560 may detect a suspected lesion region in an image and perform a precision diagnosis procedure when a suspected lesion region corresponding to a value equal to or greater than a certain threshold is detected. For example, the control unit 560 may include a diagnosis unit for analyzing a suspected lesion region in each body region and determining whether the suspected lesion region corresponds to a lesion through the diagnosis support model 550.

Also, when it is determined as a result of pre-processing of the image processing unit 520 that brightness of an image needs to be adjusted, the control unit 560 may adjust the lighting of the imaging unit 510.

The control unit 560 may calculate location information regarding body regions based on a sensing result of the sensor unit 512. Also, the control unit 560 may switch the capsule endoscope apparatus 500 to a leader mode or a follow mode set in advance, based on the location information regarding body regions.

According to another embodiment of the present disclosure, to improve the diagnostic performance of a capsule endoscope apparatus, a means for moving and absorbing/desorbing the capsule endoscope apparatus may be further provided.

Figure 9A:
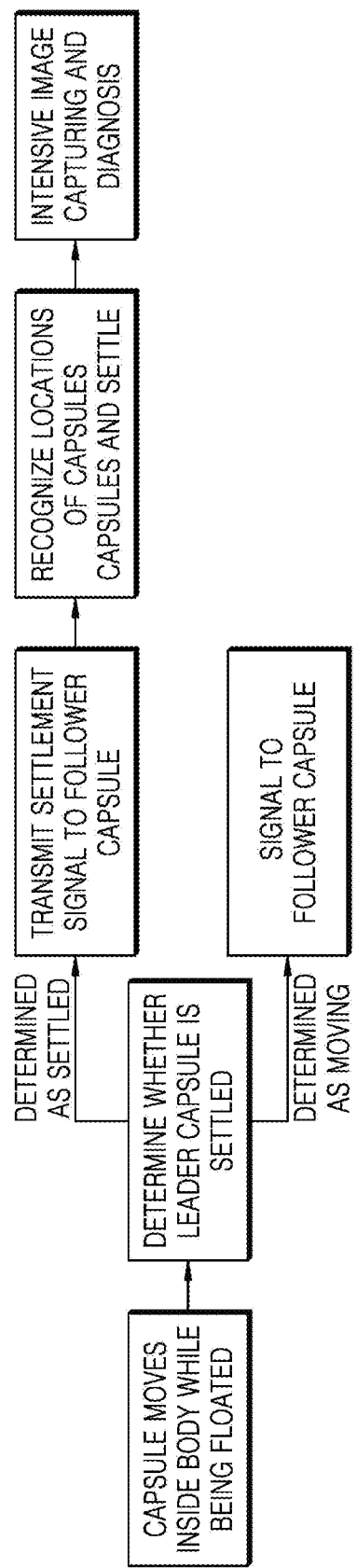
FIGS. 9A and 9B are conceptual views for describing the movement of a capsule endoscope apparatus according to an embodiment.

According to an embodiment, referring to FIG. 9A, first, a capsule endoscope apparatus may move in the body while being floated. Here, a leader capsule endoscope apparatus determines whether to accommodate based on whether a lesion is detected and may transmit a signal instructing to move to a next region or to settle to other capsule endoscope apparatuses. Here, when the leader capsule endoscope apparatus determines that accommodation is needed, each capsule endoscope apparatus may share its location information, be settled at a particular point, and intensively capture images a point that appears to be a suspected lesion region.

Figure 9B:
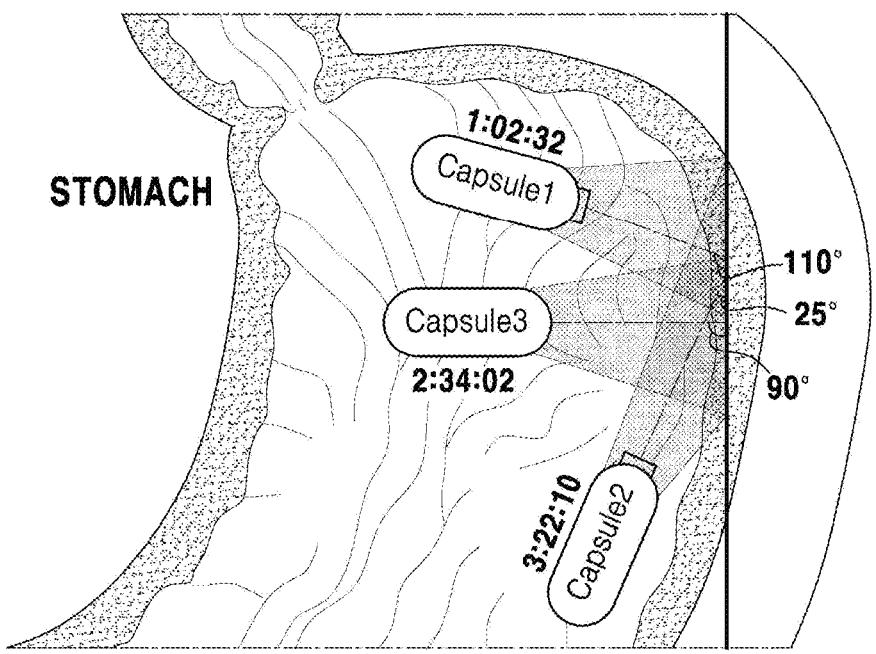

FIG. 9B shows an example in which capsule endoscope apparatuses capture a region determined as a lesion during examination time periods. Here, each capsule endoscope apparatus may capture images of the lesion at different locations and angles at different time periods during the examination time. In other words, even in the same region, respective capsule endoscope apparatuses may capture images at time points as shown in FIG. 9B. In this case, each capsule endoscope apparatus may record information regarding a suspected lesion region by using information regarding a time point and a location at which images are captured as metadata and may be settled at a particular region and intensively capture images.

Meanwhile, referring to FIG. 9B, each capsule endoscope apparatus may perform image quality improvement by controlling a lighting as an example of primary image processing. There may be darker or brighter places for each location where each capsule endoscope apparatus is settled, and when, it is determined that the brightness of captured images is not sufficient, each capsule endoscope apparatus may control the lighting to an appropriate degree to capture images with improved image quality.

According to another embodiment, capsule endoscope apparatuses may perform a collaborative process of performing lighting control or capturing images in a divided manner through role allocation. For example, a collaborative diagnosis process may be performed as each capsule endoscope apparatus may independently perform one or more functions of image capturing, lighting control, and image processing according to a pre-set collaborative process and collect results produced by a plurality of capsule endoscope apparatuses through wireless communication later. For example, a collaboration may be performed in a manner that, when one capsule endoscope apparatus illuminates a particular region by adjusting a lighting thereof, another capsule endoscope apparatus captures images of the particular region.

Figure 10A:
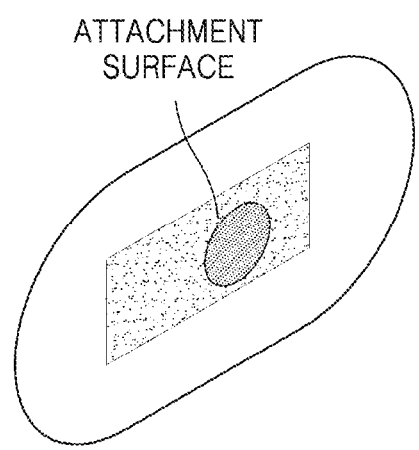
Figure 10B:
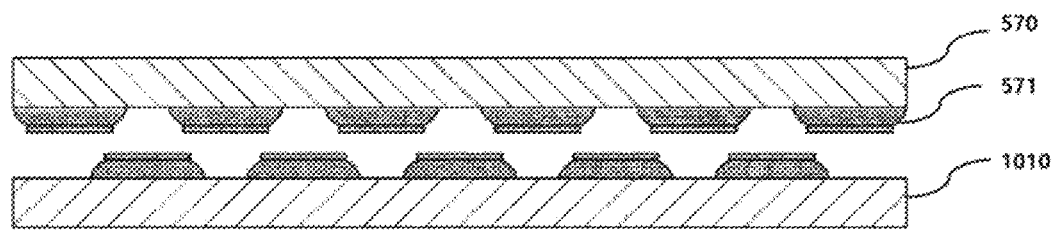
Figure 10D:
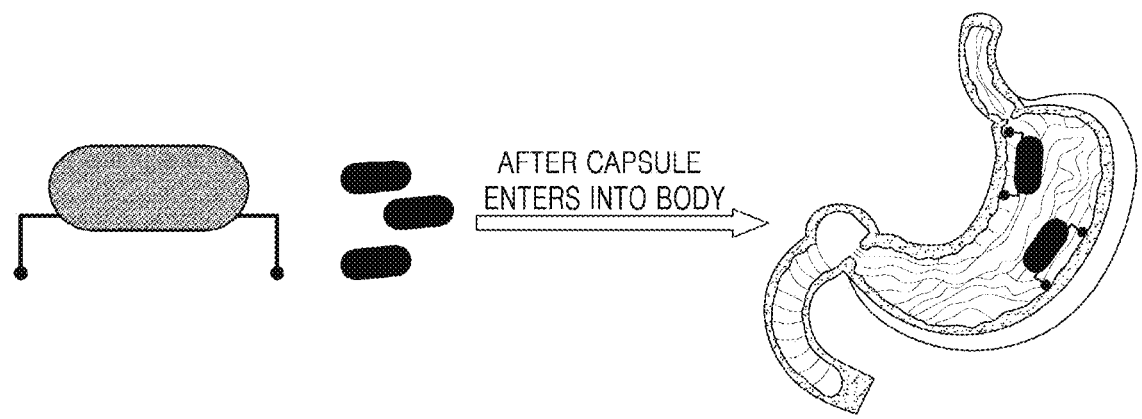
Figure 12A:
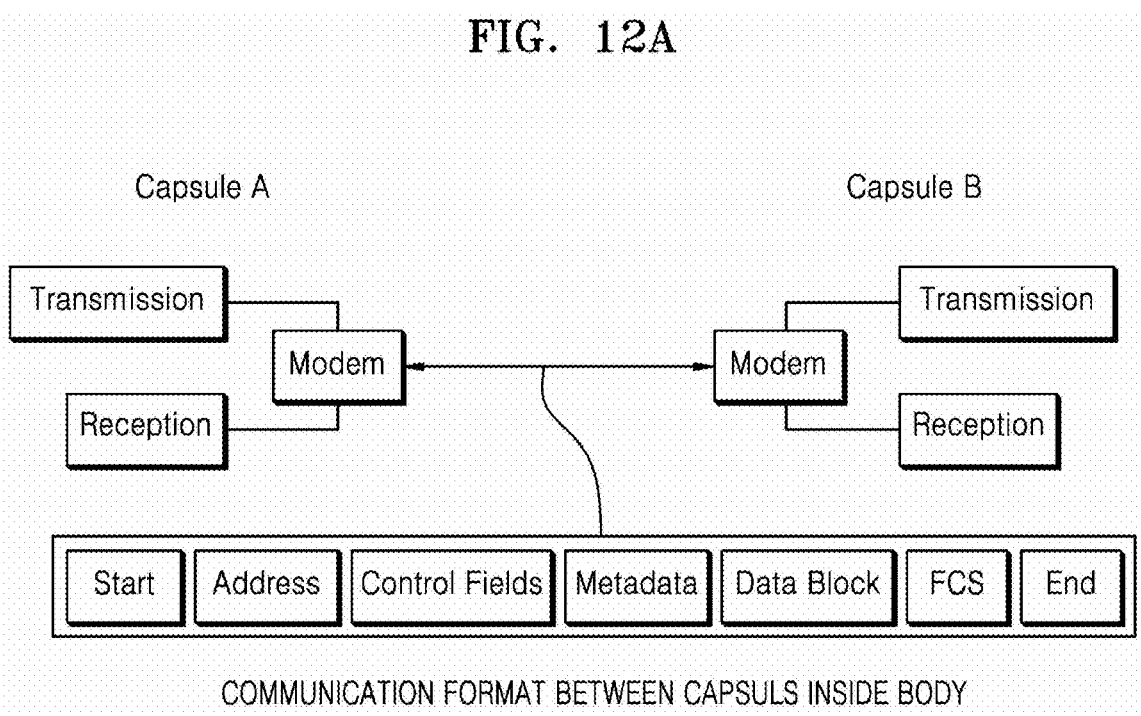
Figure 12B:
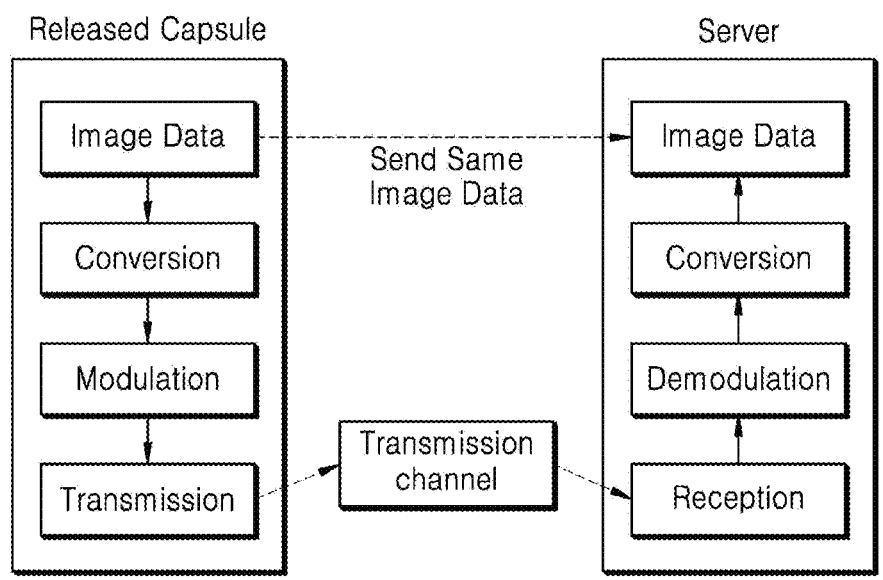

As another embodiment, movement and adsorption/desorption means of a capsule endoscope apparatus will be described below with reference to FIGS. 10A to 10D. Referring to FIG. 5, the capsule endoscope apparatus may include the adsorption/desorption unit 570 and an adsorption site and may have a moving means as shown in FIG. 10D (not shown in FIG. 5).

The adsorption/desorption unit 570 may be adsorbed to or desorbed from the inner wall of the body by adsorbing moisture from the inner wall of the body or discharging stored moisture. For example, referring to FIG. 10A, the capsule endoscope apparatus 500 may have an attachment surface for vacuum adsorption and a compression rubber. In this case, the capsule endoscope apparatus operates in the same flow as shown in FIG. 10C. First, the capsule endoscope apparatus 500 has a moisture storage unit and a moisture discharging unit (not shown) and may be absorbed to the inner wall of the body through vacuum absorption to prevent injection of the air as the moisture storage unit absorbs a liquid on an attachment. Also, after diagnostic data is collected, the capsule endoscope apparatus may be detached from the attachment surface by spraying a liquid from the moisture discharging unit.

In another example, in consideration of the characteristics of the environment inside the body in which a lot of liquid is present, wet absorption/desorption may be also performed. In the case of the inside of the body in which a lot of liquid is present, water molecules are easily injected into a gap between surfaces, and thus adhesion is difficult. Referring to FIG. 10B, according to the present disclosure, an absorption/desorption unit having concave fine structures are arranged on an adhesive surface may be provided. Also, referring to FIG. 10C, a capsule endoscope apparatus according to the present disclosure collects diagnosis data after being absorbed and may be safely absorbed/desorbed without leaving a wound by absorbing and removing the moisture of an attachment surface through a moisture storage unit and discharging the moisture through a moisture discharging unit to return the attachment surface to its original state. This is different from the above-stated vacuum absorption/desorption operation in that adsorption proceeds immediately without a separate moisture removing process.

In another example, in consideration of the characteristics of the environment inside the body in which a lot of liquid is present, wet adsorption/desorption may be also performed. In the case of the inside of the body in which a lot of liquid is present, water molecules are easily injected into a gap between surfaces, and thus adhesion is difficult. Referring to FIG. 10B, according to the present disclosure, an adsorption/desorption unit 570 having concave fine structures 571 are arranged on an adhesive surface 1010 may be provided.

According to another embodiment, the capsule endoscope apparatus 500 according to the present disclosure may utilize a more active means of movement. Referring to FIG. 10D, the capsule endoscope apparatus may be implemented to have legs capable of performing movement. In this case, the capsule endoscope apparatus may move by itself in the form of crawling. In this case, the capsule endoscope apparatus may be designed to have a structure in which legs are folded before oral administration and the corresponding legs are unfolded when the capsule endoscope apparatus enters the body. In this case, as compared to a conventional capsule endoscope apparatus that is only moved by the peristalsis of the digestive system, more active movement may be implemented. Here, since the capsule endoscope is capable of moving around the inside of an organ, rubber foot plates or suction plates may be used to prevent a wound on the inner wall of the body.

Referring back to FIG. 5, the capsule endoscope apparatus 500 may include the diagnosis support model 550. In the present disclosure, since it is necessary to extract and process a great amount of images into medically effective data, the pre-trained diagnosis support model 550 is needed. According to the present disclosure, a diagnosis support model may be trained with lesion image data through a machine learning-based modeling method, and image data obtained by a capsule endoscope apparatus itself may be determined and processed based on the trained diagnosis support model.

To this end, the image processing unit 520 may process images during a precision diagnosis procedure. For example, the image processing unit 520 may perform pre-processing on images obtained by the imaging unit 510. Next, the image processing unit 520 may classify input images according to respective regions of the body, such as the stomach, the small intestine, and the large intestine. Also, the image processing unit 520 classifies image data including a suspected lesion region and image data without a suspected lesion region and performs pre-processing of each data. During a pre-processing operation, old data, data with significantly abnormal values, and missing data may be checked and excluded from a data set or processed, and it may be necessary to perform a unique pre-processing operation for each organ in the body.

In another example, the image processing unit 520 may perform processing of registering a second image including information regarding a suspected lesion region with one or more first images. In detail, image processing unit 520 may process one or more first images by down-sampling the one or more first images, extracting feature points, and matching the extracted feature points with features of a base image.

In another example, the image processing unit 520 may register an omni-view image from a plurality of images having a plurality of viewpoints.

Next, the diagnosis support model 550 of the capsule endoscope apparatus 500 may use a K-fold cross-validation technique to construct and evaluate a diagnosis model as shown in FIG. 11. FIG. 11 is a conceptual diagram showing pre-processed image data divided into five data folds. There may be a train set for each data fold, and the K-fold cross-validation technique may obtain an optimal diagnosis model by combining train data and data at various ratios and cross-evaluate combined data to increase the accuracy of a diagnosis model. According to the present disclosure, by utilizing all data sets for evaluation and training, the utilization of the data sets and accuracy of a diagnosis model may be increased to more accurately determine a lesion region. Although data is divided into five folds in the embodiment of FIG. 11, K, the number of folds, is not limited thereto, and data may be divided differently and learned depending on environmental variables, such as the location of a lesion to learn or a capsule endoscope model used.

Also, although the K-fold cross-validation technique is exemplified in the present disclosure, the present disclosure is not limited thereto, it should be considered that techniques having some differences therefrom are also within the scope of the present disclosure as long as the purpose of the present disclosure is specifically implemented.

Figure 13:
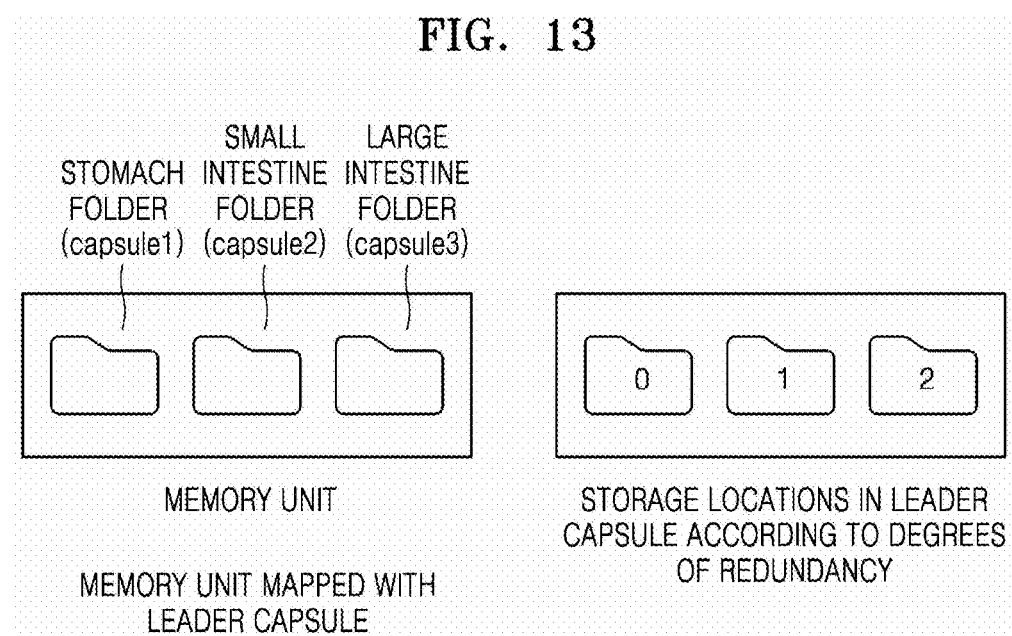
FIG. 13 shows an example of a method by which a capsule endoscope apparatus stores data in a memory according to an embodiment.

FIG. 13 shows an example of a method by which a capsule endoscope apparatus stores data in a memory according to an embodiment. For example, the capsule endoscope apparatus according to the present disclosure may include the storage unit 540. Alternatively, the storage unit 540 may be referred to as a memory, because the storage unit 540 serves to store and retain data.

Referring to FIG. 13, the storage unit 540 may classify images according to body regions and store classified images in different folders. In another example, a large number of images may be transmitted and received between a plurality of capsule endoscope apparatuses, and a capsule endoscope apparatus may classify and store a plurality of images (or videos) received from other capsule endoscope apparatuses according to degrees of redundancy and utilize the plurality of images as data for image processing. In another example, a capsule endoscope apparatus may store images processed by the image processing unit 520 only when the capsule endoscope apparatus is in the leader mode in a corresponding region. According to such a memory management method, a capsule endoscope apparatus may store only image data having medical information from images captured for a long time period and, by classifying and managing the SAME according to body regions, may perform memory management efficiently and optimally. Here, although the term "folder" is used, it may be considered that terms referred to as otherwise have similar technical definitions as long as being suitable for classifying and storing captured images.

Referring to FIGS. 5 and 13, a communication module 530 of the capsule endoscope apparatus 500 may transmit/receive images processed to/from another capsule endoscope apparatus or a terminal by using a wireless communication method.

For example, the communication module 530 may transmit/receive data to/from other capsule endoscope apparatuses inside the body. Here, the data may include processed images, location information, meta information, etc. In another example, the communication module 530 may receive one or more processed first images from another capsule endoscope apparatus during a precision diagnosis procedure.

For example, the wireless communication method may include an RF communication method, a human body communication (HBC) method, etc. Although data communication may be performed stably through an RF communication, large power consumption is needed to transmit a large amount of data at a high speed. Although data may be transmitted at a high speed with low power in a HBC communication, electrodes need to stably contact the body for stable communication. Therefore, the RF communication method and the HBC method may be used together.

Also, the communication module 530 may transmit data stored in a capsule endoscope apparatus to a user terminal or a medical service platform through wireless communication when an examination is completed and the capsule endoscope apparatus is discharged.

FIG. 13B shows a structure in which a capsule endoscope apparatus performs unidirectional communication with a user terminal or a medical institution management server. FIG. 13C is a conceptual diagram showing that a capsule endoscope apparatus transmits collected data to a medical institution.

FIG. 13A shows a format for performing communication between capsule endoscope apparatuses inside the body. A capsule endoscope apparatus A and a capsule endoscope apparatus B may perform bidirectional communication through communication modules thereof. Here, a data format may include a control field, meta data, data blocks, FCS, etc., between a start point and an end point. Here, the metadata may include location information regarding capsule endoscope apparatuses, data regarding image captured time points, data regarding a lesion, etc.

The communication module 530 may use a full-duplex communication method capable of performing transmission and reception simultaneously, thereby communicating with a plurality of capsule endoscope apparatuses connected to a communication channel. Also, the communication module 530 may use a half-duplex communication method, which is a low-power communication method for performing transmission and reception according to time.

The bidirectional communication method of the communication module 530 enables a plurality of capsule endoscope apparatuses to have a cooperative relationship therebetween for transmitting and sharing data regarding suspected lesion regions detected by the respective capsule endoscope apparatuses and images processed by the respective capsule endoscope apparatuses to one another. Also, each capsule endoscope apparatus may transmit its location information to other capsule endoscope apparatuses, thereby cooperating with the other capsule endoscope apparatuses to obtain more imaging data from various angles during a precision diagnosis procedure. Also, since an error may occur in data exchange when there is a time difference during a communication process, the communication module 530 may use a synchronous transmission method capable of receiving data by correcting the time difference. For example, bits may be transmitted block-by-block by using flags indicating the start and the end of transmission data in a bit-oriented synchronization method. As the bidirectional communication method, any communication method that enables data transmission and reception by using low-cost and low-power devices may be used without being limited to a full-duplex communication method or a half-duplex communication method. Communications between capsule endoscope apparatuses in the body may be implemented in various methods other than the above-stated communication methods.

The capsule endoscope apparatus 500 may repeatedly perform image capturing, diagnosis, and image processing while moving in the body, and, after being discharged, the capsule endoscope apparatus may transmit stored data to a user terminal or a platform of a medical institution. FIGS. 13B and 13C are diagrams showing communication structures in which the capsule endoscope apparatus 500 according to the present disclosure transmits data to a platform or a server of a medical institution by using a wireless communication method.

As compared to the conventional capsule endoscopy performed only at medical institutions, a capsule endoscope apparatus according to the present disclosure may automatically perform a part of a lesion diagnosis and process images without the presence of a medical staff, and thus it is not necessary to go to a medical institution to check a diagnosis result. Therefore, a capsule endoscope apparatus according to the present disclosure may transmit data refined through image processing to a platform of the corresponding medical institution or a user terminal even after a subject is discharged from a hospital. In this case, the subject does not have to wait at the hospital for a long time until the capsule endoscope apparatus to be discharged, and the convenience of diagnosis may be significantly improved.

To this end, the communication module 530 of the capsule endoscope apparatus 500 may perform unidirectional communication as shown in FIG. 13B, and a capsule endoscope apparatus may wirelessly transmit data to a platform (or a management server) of a medical institution or a user terminal. For example, the communication module 530 may convert data stored in the storage unit 540 into digital signals and perform long-distance wireless communication through a high-frequency modulation process. At this time, since the capsule endoscope apparatus has already been discharged from the body, a long-distance wireless communication may be performed, and various communication methods capable of safely transmitting a large amount of data at once without loss may be used.

According to another embodiment, since a capsule endoscope apparatus according to the present disclosure handles sensitive data such as personal medical information, an encryption method may be applied to data transmission. For example, to guarantee the reliability of data, various methods like 3-way handshaking may be applied to a process of checking connection between devices performing communication according to a bidirectional communication technique or a communication control protocol in which data transmission may be confirmed with ACK.

Figure 14A:
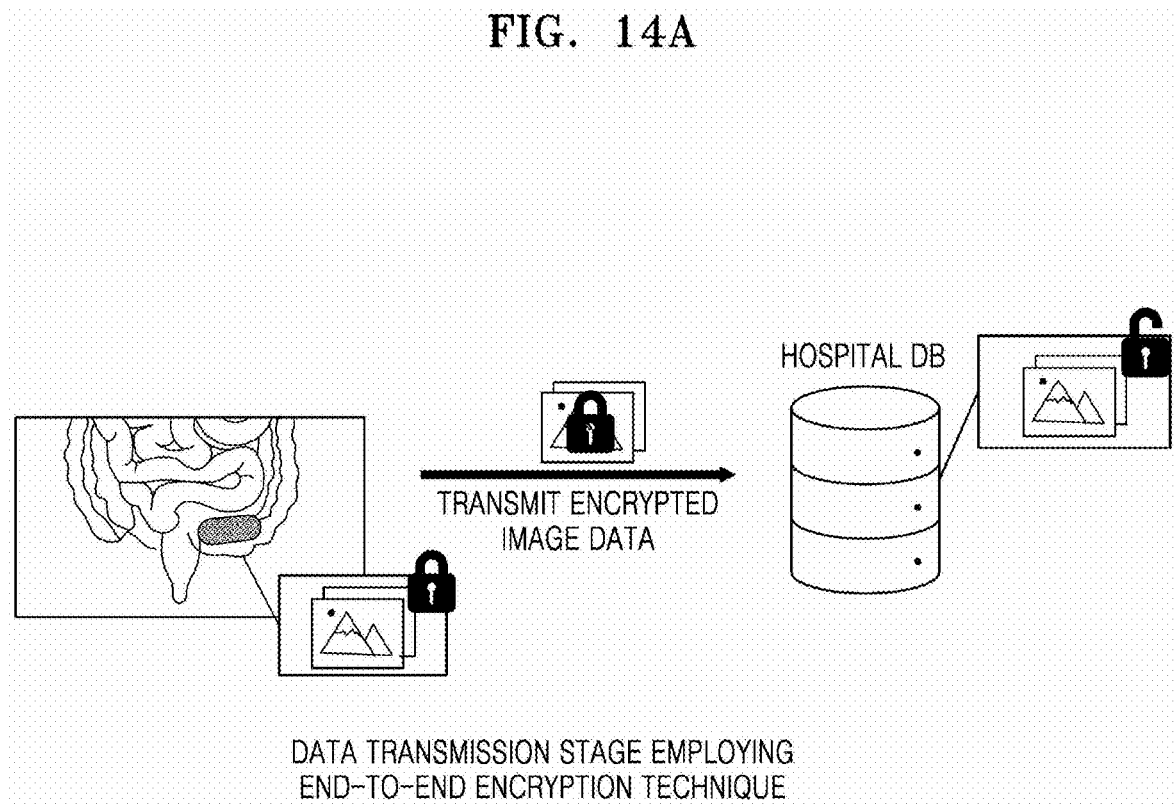
FIGS. 14A and 14B are conceptual views for describing application of encryption technology in data communication according to another embodiment.
Figure 14B:
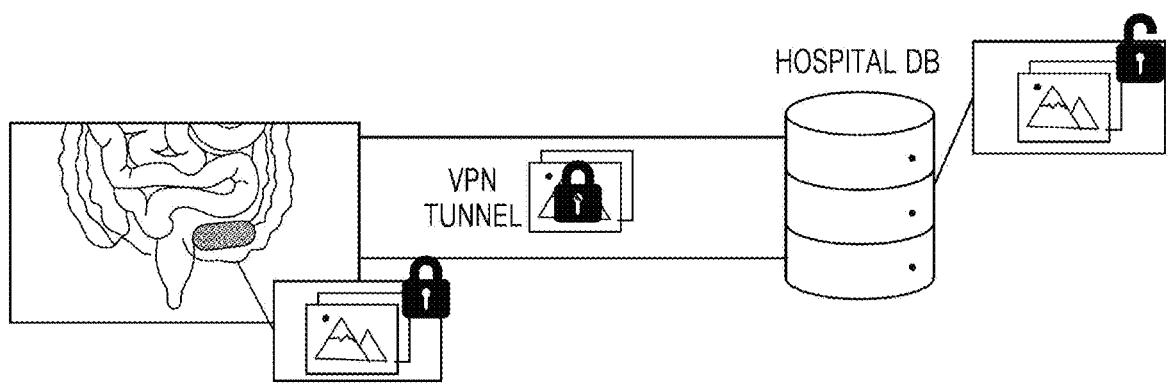

In another example, technologies such as an end-to-end encryption and a VPN may be used as shown in FIGS. 14A and 14B for secure information delivery in a data transmission operation.

FIGS. 14A and 14B are conceptual views for describing application of encryption technology in data communication according to another embodiment. Referring to FIG. 14A, the communication module 530 of the capsule endoscope apparatus 500 may detect location information regarding a location at which the capsule endoscope apparatus 500 is discharged, encrypt data stored in the storage unit 540, and transmit encrypted data to a management server. Such an encryption technique guarantees the safety and the reliability of data transmission, because encrypted data cannot be decrypted without information regarding a key (a private key, a public key, a secret key, etc.) stored in a capsule endoscope apparatus. Referring to FIG. 14B, the communication module 530 of the capsule endoscope apparatus 500 may perform more secure data transmission by further securing encrypted data once more by using a VPN.

In case of transmitting encrypted data from the start of data transmission, even when data is stolen by an attack like sniffing, the data is safe because the data cannot be decrypted without key information stored in the capsule endoscope apparatus.

Figure 15A:
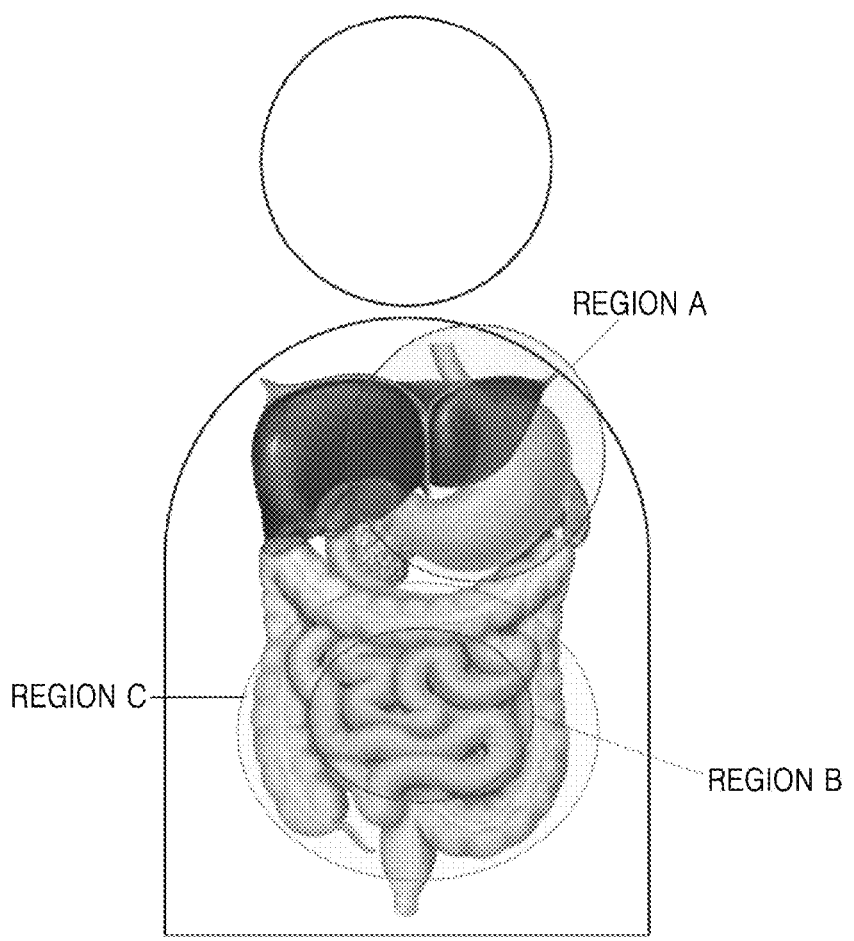
FIGS. 15A and 15B shows an example of generating a body map of a body according to another embodiment.
Figure 15B:
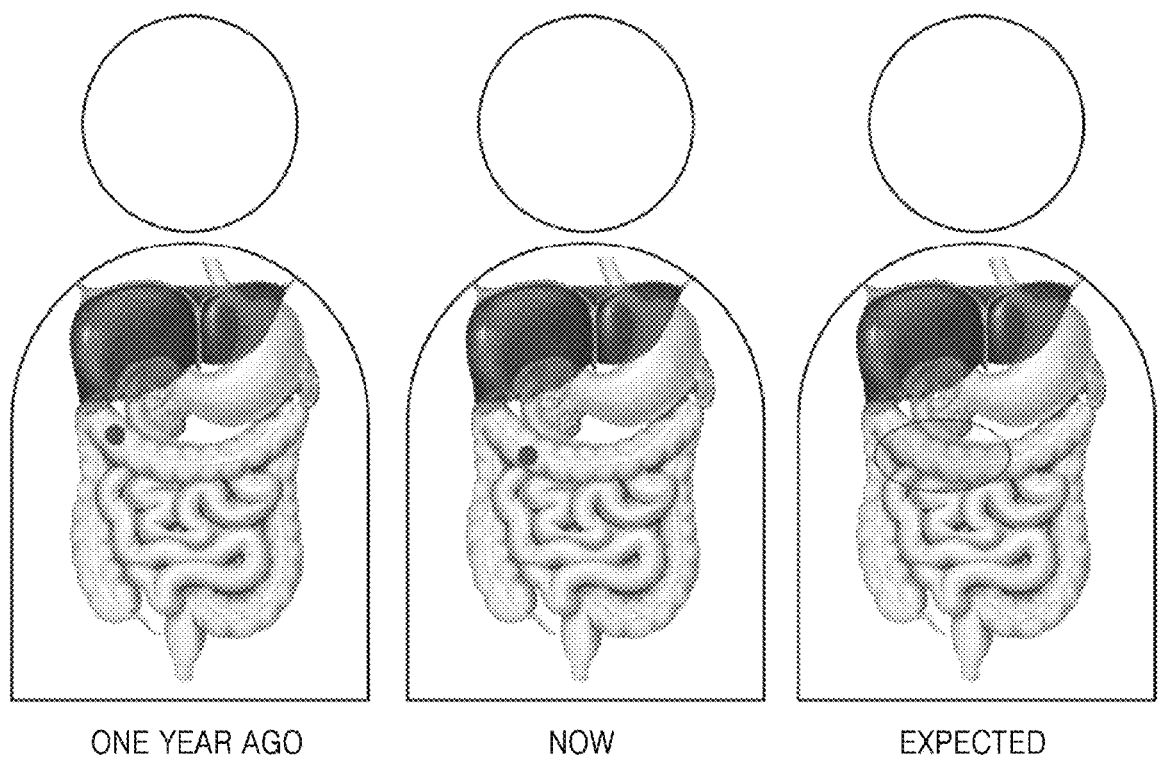

FIGS. 15A and 15B shows an example of generating a body map of a body according to another embodiment. An examination using a capsule endoscope apparatus according to the present disclosure may calculate location information regarding body regions. By using the location information, a medical service platform of a medical institution or a device may register a user-customized body map by mapping the location information to a human body map. Referring to FIG. 15A, a medical service platform may divide a human body into about three regions (region A, region B, and region C) based on major organs. An examiner and a subject may more quickly and conveniently check a point at which a suspected lesion region is detected based on a body map. Also, when a subject cumulatively receives an endoscopy examination using capsule endoscope apparatus a number of times, a change in the state of a lesion may be more easily tracked based on accumulated data. When a lesion is diagnosed as a simple polyp by the diagnosis of a medical staff, information regarding related diseases or health conditions may be provided to a user. FIG. 15B is a diagram showing that an expected location of a lesion in the next year may be predicted based on locations of a lesion in the past year and a current lesion.

According to another embodiment, FIG. 16 is a conceptual diagram for describing providing a diagnosis result to a user through interconnection with a mobile platform according to another embodiment. Referring to FIG. 16, a result of supporting a lesion diagnosis by a capsule endoscope apparatus according to the present disclosure may be transmitted to a user through a medical service platform. For example, when the medical service platform provides information to a user through a mobile device, as shown in FIG. 16, an examination status, medical records and related tips, information regarding health care, etc. may be provided together with a result of a diagnosis using a capsule endoscope apparatus according to the present disclosure. For example, in this case, a subject may check a result of a lesion diagnosis by a capsule endoscope apparatus directly through a medical service platform without visiting a medical institution, and, when a medical staff inputs medical opinions through the corresponding medical service platform, a remote medical service, etc. may be supported.

The embodiments described above may be implemented with a hardware component, a software component, and/or a combination of a hardware component and a software component. For example, devices, methods, and components described in the embodiments may be implemented by using one or more general-purpose computers or a special-purpose computer, such as, for example, a processor, a controller, an arithmetic logic unit (ALU), a digital signal processor, a microcomputer, a field programmable gate array (FPGA), a programmable logic unit (PLU), a microprocessor, or another device capable of executing and responding to instructions. The processor may execute operating system (OS) and one or more software applications that are executed on the OS. Also, the processor may access, store, control, process, and create data in response to execution of software. Although one processing device is used in some of the descriptions given above for convenience of understanding, one of ordinary skill in the art will understand that the processing device may include a plurality of processing elements and/or a plurality of types of processing elements. For example, the processing device may include a plurality of processors or one processor and one controller. Also, other processing configurations such as a parallel processor may be employed.

According to the above-described solution of the present disclosure, the present disclosure may implement automation of a diagnosis supporting method through a collaborative process between a plurality of capsule endoscope apparatuses. For example, in the case of a conventional capsule endoscope apparatus, a diagnosis is still made based on real-time control of a doctor. However, according to the present disclosure, images captured by respective capsule endoscope apparatuses are registered into one image to improve the accuracy of lesion diagnosis results, and, since a diagnosis result may be provided without the presence of a medical staff throughout an endoscopy diagnosis process, convenience of a diagnosis may be maximized.

Also, the present disclosure applies diagnosis technology using lesion data learned in advance based on artificial intelligence and a capsule endoscope apparatus is capable of determining a body region by itself, thereby significantly contributing to the intelligence of a capsule endoscope apparatus. For example, a process in which a plurality of capsule endoscope apparatuses collaborate with one another to produce a single result may significantly improve the accuracy of a lesion diagnosis.

Also, according to the present disclosure, the efficiency in a diagnosis and an examination using a capsule endoscope apparatus may be maximized. For example, a capsule endoscope apparatus according to the present disclosure may reduce the amount of power consumed by other conventional capsule endoscope apparatuses by transmitting data to the outside the body in real time. According to an embodiment of the present disclosure, a precision diagnosis supporting procedure is performed based on minimal collaborative communication between a plurality of capsule endoscope apparatuses, and a processed precision diagnosis result is transmitted to a user terminal or a medical institution, thereby minimizing power consumption for each stage of a diagnosis. Also, according to another embodiment of the present disclosure, images in which a lesion is not detected are immediately deleted or, even when a suspected lesion region is detected, a capsule endoscope apparatus operating in the leader mode collects and processes data regarding the suspected lesion region, thereby implementing role sharing and efficiency for data management.

According to embodiments of the present disclosure, images whose brightness is adjusted through lighting control in primary image processing may be obtained, and, by sharing data captured by a plurality of capsule endoscope apparatuses during secondary image processing, image quality improvement through a diversity effect may be provided. Therefore, significantly improved image processing as compared to a conventional capsule endoscope apparatus may be performed, thereby significantly improving the accuracy of a lesion diagnosis.

The present disclosure focuses on a collaborative process between a plurality of capsule endoscope apparatuses, thus being distinguished from researches and developments of conventional capsule endoscope apparatuses focusing on communication inside the body. Unlike the conventional capsule endoscope apparatus focusing on real-time communication to the outside of the body, the present disclosure proposes embodiments for obtaining images already having high-quality when obtained by obtaining an omni-view video by differently configuring a camera module of an imaging unit of a capsule endoscope apparatus or controlling a lighting.

From the social point of view, a diagnosis supporting technology using existing endoscope apparatuses has a problem in terms of user convenience, because the entire process is fundamentally controlled by a medical staff (person). However, according to the present disclosure, the entire process may be automatically performed by a plurality of capsule endoscope apparatuses, and a diagnosis result is transmitted directly to a user terminal or a medical institution. Therefore, a user does not have to be examined or wait in a hospital while an endoscopy examination is being performed, thereby significantly contributing to the commercialization of lesion diagnosis technology through endoscope apparatuses.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A capsule endoscope apparatus for supporting lesion diagnosis, the capsule endoscope apparatus comprising:
   an imaging unit configured to capture one or more images of an inside of a body;

a control unit configured to detect a suspected lesion region in the images and perform a precision diagnosis procedure when a suspected lesion region corresponding to a value equal to or greater than a certain threshold is detected;

an adsorption/desorption unit capable of being attached to inner wall of a body in conjunction with fine structure of adhesive surface and being taken off from the inner wall by removing moisture of the adhesive surface through moisture adsorption and restoring the adhesive surface to a shape before the attachment through moisture discharge;

an image processing unit configured to process the images in the precision diagnosis procedure; and a communication module configured to transmit and receive processed images to another capsule endoscope apparatus or a terminal by using a wireless communication method.

2. The capsule endoscope apparatus of claim 1, wherein the image processing unit performs pre-processing on images captured by the imaging unit in the precision diagnosis procedure, and the control unit further comprises a diagnosis unit configured to analyze a suspected lesion region based on a location information regarding body regions and diagnose whether the suspected lesion region corresponds to a lesion.

3. The capsule endoscope apparatus of claim 2, wherein, when it is determined to adjust brightness of an image as a result of the pre-processing, the control unit adjusts a lighting of the imaging unit.

4. The capsule endoscope apparatus of claim 1, wherein the communication module receives one or more processed first images from other capsule endoscope apparatuses in the precision diagnosis procedure, and the image processing unit performs a process of registering a second image comprising information regarding the suspected lesion region with the one or more first images.

5. The capsule endoscope apparatus of claim 4, wherein the image processing unit registers the second image by down-samples the one or more first images to extract feature points and matching the extracted feature points with features of a base image.

6. The capsule endoscope apparatus of claim 1, further comprising:

a sensor unit comprising at least one of a geomagnetic sensor, an acceleration sensor, and a timer sensor, wherein the control unit calculates location information regarding body regions based on a sensing result of the sensor unit.

7. The capsule endoscope apparatus of claim 6, wherein, in the precision diagnosis procedure, the control unit switches to a leader mode or a follow mode set in advance based on the location information regarding body regions, and the communication module receives processed first images from another capsule endoscope apparatus when the capsule endoscope apparatus is in a leader mode and transmits processed first images to another capsule endoscope apparatus when the capsule endoscope apparatus is in a follow mode.

8. The capsule endoscope apparatus of claim 1, wherein imaging unit comprises multi-camera modules arranged at different locations to capture images having a plurality of viewpoints, and the image processing unit generates an omni-view image from the plurality of images having a plurality of viewpoints.

9. A method of supporting lesion diagnosis, the method comprising:

capturing one or more images of an inside of a body;

detecting a suspected lesion region in the images and performing a precision diagnosis procedure when a suspected lesion region corresponding to a value equal to or greater than a certain threshold is detected;

attaching to an inner wall of a body in conjunction with fine structure of an adhesive surface and taking off from the inner wall by removing moisture of the adhesive surface through moisture absorption and restoring the adhesive surface to a shape before the attachment through moisture discharge;

processing the images in the precision diagnosis procedure; and transmitting and receiving processed images to or from another capsule endoscope apparatus or a terminal by using a wireless communication method.

10. The method of claim 9, wherein, in the processing of the images, pre-processing is performed on the captured images, and the method further comprises analyzing a suspected lesion region based on a location information regarding body regions and diagnosing whether the suspected lesion region corresponds to a lesion.

11. The method of claim 10, further comprising adjusting a lighting of an imaging unit when it is determined as a result of the preprocessing that brightness of images need to be adjusted.

12. The method of claim 9, further comprising:

switching to a leader mode or a follow mode set in advance based on the location information regarding body regions;

receiving processed first images from another capsule endoscope apparatus in the leader mode; and registering, with received one or more first images, a second image comprising information regarding the suspected lesion region.

13. The method of claim 12, wherein, in the registering the second image, the second image is registered by down-sampling the first images to extract feature points and matching the extracted feature points with features of a basic image.

14. A computer-readable recording medium having recorded thereon a program for executing the method of claim 9 on a computer.

* * * * *